(12) United States Patent (10) Patent No.: US 7,638,765 B1
Belford et al. (45) Date of Patent: Dec. 29, 2009

(54) FAIMS CELL WITH SEPARATE DESOLVATION AND CARRIER GAS INLETS

(75) Inventors: Michael W. Belford, Los Altos, CA (US); Jean Jacques Dunyach, San Jose, CA (US)

(73) Assignee: Thermo Finnigan LLC, San Jose, CA (US)

( * ) Notice: Subject to any disclaimer, the term of this patent is extended or adjusted under 35 U.S.C. 154(b) by 277 days.

(21) Appl. No.: 11/829,489

(22) Filed: Jul. 27, 2007

(51) Int. Cl.
    *H01J 49/40* (2006.01)
(52) U.S. Cl. .................. 250/290; 250/281; 250/282; 250/292; 250/294
(58) Field of Classification Search .............. 250/288, 250/290, 292, 294
    See application file for complete search history.

(56) References Cited

U.S. PATENT DOCUMENTS

| | | | |
|---|---|---|---|
| 5,420,424 A | 5/1995 | Carnahan et al. | |
| 6,504,149 B2 | 1/2003 | Guevremont et al. | |
| 6,703,609 B2 | 3/2004 | Guevremont et al. | |
| 6,753,522 B2 | 6/2004 | Guevremont et al. | |
| 6,774,360 B2 | 8/2004 | Guevremont et al. | |
| 6,987,262 B2 | 1/2006 | Guevremont | |
| 7,005,633 B2 | 2/2006 | Guevremont et al. | |
| 7,026,612 B2 | 4/2006 | Guevremont et al. | |
| 7,034,286 B2 | 4/2006 | Guevremont et al. | |
| 7,135,674 B2 | 11/2006 | Guevremont et al. | |
| 7,189,966 B2 | 3/2007 | Syms | |
| 7,217,921 B2 | 5/2007 | Guevremont et al. | |
| 7,227,132 B2 | 6/2007 | Guevremont et al. | |
| 7,351,960 B2 * | 4/2008 | Belford ...................... 250/288 |
| 7,468,511 B2 * | 12/2008 | Belford ...................... 250/290 |
| 7,550,717 B1 * | 6/2009 | Belford et al. .............. 250/281 |

* cited by examiner

*Primary Examiner*—David A Vanore
(74) *Attorney, Agent, or Firm*—Charles B. Katz; Thomas F. Cooney

(57) ABSTRACT

A method for analyzing ions includes providing a desolvation chamber in communication with an analytical gap of a FAIMS analyzer, via an ion inlet orifice. A flow of ions is introduced into the desolvation chamber along a flow path that is toward the ion inlet orifice and into the analytical gap of the FAIMS analyzer. A flow of a desolvation gas is provided into the desolvation chamber via a first gas inlet, such that a portion of the flow of the desolvation gas is countercurrent to the flow of ions. A flow of a carrier gas is provided separately via a second gas inlet, which is defined downstream relative to the desolvation chamber. In particular, the composition of the carrier gas is different than the composition of the desolvation gas. Accordingly, the flow of the carrier gas is provided substantially into the analytical gap for transporting ions along a path between the ion inlet orifice and an ion outlet orifice of the analytical gap.

18 Claims, 15 Drawing Sheets

FAIMS CELL WITH SEPARATE DESOLVATION AND CARRIER GAS INLETS

FIELD OF THE INVENTION

The instant invention relates generally to High Field Asymmetric Waveform Ion Mobility Spectrometry (FAIMS), and more particularly to a FAIMS cell having separate desolvation and carrier gas inlets.

BACKGROUND OF THE INVENTION

High Field Asymmetric Waveform Ion Mobility Spectrometry (FAIMS) is a technology that is capable of separating gas-phase ions at atmospheric pressure. In FAIMS, the ions are introduced into an analytical gap across which a radio frequency (rf) waveform, the magnitude of which is referred to as dispersion voltage (DV), is applied such that the ions are alternately subjected to high and low electric fields. The waveform is asymmetric; the high field is typically applied for one time unit followed by an opposite-polarity low field of half the high field component that is applied for twice as long. The field-dependent change in the mobility of the ions causes the ions to drift toward the walls of the analytical gap. Since the dependence of ion mobility on electric field strength is compound specific, this leads to a separation of the different types of ions one from the other, and is referred to as the FAIMS separation or the FAIMS mechanism. In order to transmit an ion of interest through FAIMS, an appropriate direct current compensation voltage (CV) is applied to compensate for the drift of the ion of interest toward the analyzer wall. By varying the CV, different ions are selectably transmitted through the FAIMS device.

Certain types of ionization sources, such as for instance an electrospray ionization source (ESI), are known to produce ions that are highly solvated. When these highly solvated ions are introduced into the FAIMS analytical gap some of the solvent evaporates from around the ions, thereby contaminating the carrier gas that is flowing through the FAIMS. Unfortunately, FAIMS is highly sensitive to moisture as well as contaminants in the gas that is entering the analytical gap. In fact, frequently contaminants or too much water vapor will result in complete loss of signal and failure of the FAIMS to function properly. Since electrospray ionization involves the high-voltage-assisted-atomization of a solvent mixture, the resulting ion plume contains an amount of water and other volatile solvents that is far too high to be tolerated in FAIMS.

In U.S. Pat. No. 6,770,875, the entire contents of which are incorporated herein by reference, Guevremont et al. teach an ESI-FAIMS combination including a separate desolvation chamber that is disposed between the ESI chamber and the ion inlet orifice of the FAIMS. The desolvation chamber includes a gas inlet orifice and a gas outlet orifice, for providing a gas flow along a direction that is approximately transverse to the direction in which the ions travel between the ESI source and the ion inlet orifice of the FAIMS. A first portion of the gas flow, which is referred to as the counter-current of gas, enters the ESI chamber so as to desolvate the ions and carry neutral solvent molecules away from the ion inlet orifice of the FAIMS. The remainder of the gas flow enters the FAIMS via the ion inlet orifice and serves as the carrier gas for transporting ions within the FAIMS analyzer between the ion inlet orifice and an ion outlet orifice thereof. In practice, often a 50:50 $He/N_2$ carrier gas/desolvation gas mixture is provided into the desolvation chamber; the gas mixture performs both the ion desolvation and ion transport functions that are required for optimal FAIMS operation. Unfortunately, using a flow of a mixed gas for desolvating ions as well as for transporting the ions through the FAIMS analytical gap leads to high consumption of the more expensive carrier gas component.

There exists a need for a FAIMS apparatus and method that overcomes at least some of the above-mentioned limitations.

SUMMARY OF EMBODIMENTS OF THE INVENTION

According to an aspect of the invention there is provided a field asymmetric ion mobility spectrometer (FAIMS) apparatus, comprising: an ionization source for producing ions from a sample; an analyzer region comprising a first electrode and a second electrode disposed in a spaced-apart facing relationship one relative to the other so as to define an analytical gap therebetween, there being an ion inlet orifice defined through a first portion of the second electrode for supporting ion introduction into the analytical gap; a desolvation chamber disposed intermediate the ionization source and the analyzer region, such that ions that are produced by the ionization source travel downstream along an ion flow path through the desolvation chamber and into the analytical gap via the ion inlet orifice; a first gas conduit extending between an inlet end that is coupleable to a desolvation gas source and an outlet end that opens into the desolvation chamber, the first gas conduit for providing a flow of a desolvation gas into the desolvation chamber; and, a second gas conduit extending between an inlet end that is coupleable to a carrier gas source and an outlet end that is open adjacent to a portion of the ion flow path that is defined downstream relative to the desolvation chamber, the second gas conduit for providing a flow of a carrier gas separately from the flow of the desolvation gas, wherein the composition of the desolvation gas is different than the composition of the carrier gas.

According to another aspect of the invention there is provided a field asymmetric ion mobility spectrometer (FAIMS) apparatus, comprising: a desolvation chamber for receiving ions from an ionization source, there being a first gas inlet defined through a portion of the desolvation chamber for supporting introduction of a flow of a desolvation gas into the desolvation chamber; a first electrode having a first electrode surface; a second electrode having a second electrode surface, the second electrode being spaced-apart from the first electrode and disposed relative to the first electrode such that the second electrode surface faces the first electrode surface so as to define an analytical gap therebetween, an ion inlet orifice being defined within a portion of the second electrode for providing fluid communication between the desolvation chamber and the analytical gap, the ion inlet orifice for receiving ions into the analytical gap, the second electrode further comprising a gas conduit defined through a portion thereof and extending between a first end that opens into the ion inlet orifice and a second end that is in communication with a source of a carrier gas, for providing a flow of a carrier gas separately from the flow of the desolvation gas.

According to another aspect of the invention there is provided a method, comprising: providing a desolvation chamber that is in fluid communication with an analytical gap of a FAIMS analyzer via an ion inlet orifice; introducing a flow of ions into the desolvation chamber along a flow path that is directed toward the ion inlet orifice and into the analytical gap of the FAIMS analyzer; providing a flow of a desolvation gas into the desolvation chamber via a first gas inlet such that a portion of the flow of the desolvation gas is counter-current to the flow of ions, so as to effect at least partial desolvation of the ions; providing separately a flow of a carrier gas via a second gas inlet that is defined downstream relative to the desolvation chamber, the composition of the carrier gas being different than the composition of the desolvation gas, and the flow of the carrier gas being provided substantially into the analytical gap for transporting ions along a path between the ion inlet orifice and an ion outlet orifice of the analytical gap.

BRIEF DESCRIPTION OF THE DRAWINGS

Exemplary embodiments of the invention will now be described in conjunction with the following drawings, in which similar reference numerals designate similar items:

FIG. 2b is an enlarged view showing the ion inlet configuration of the FAIMS apparatus of FIG. 2a;

FIG. 2c is an enlarged view showing a first alternative ion inlet configuration of the FAIMS apparatus of FIG. 2a;

FIG. 2d is an enlarged view showing a second alternative ion inlet configuration of the FAIMS apparatus of FIG. 2a;

FIG. 3b is an enlarged view showing the ion inlet configuration of the FAIMS apparatus of FIG. 3a;

FIG. 3d is an enlarged view showing an alternative ion inlet configuration of the FAIMS apparatus of FIG. 3a;

FIG. 4b is an enlarged view showing the ion inlet configuration of the FAIMS apparatus of FIG. 4a;

DESCRIPTION OF EMBODIMENTS OF THE INSTANT INVENTION

The following description is presented to enable a person skilled in the art to make and use the invention, and is provided in the context of a particular application and its requirements. Various modifications to the disclosed embodiments will be readily apparent to those skilled in the art, and the general principles defined herein may be applied to other embodiments and applications without departing from the spirit and the scope of the invention. Thus, the present invention is not intended to be limited to the embodiments disclosed, but is to be accorded the widest scope consistent with the principles and features disclosed herein.

Figure 1:
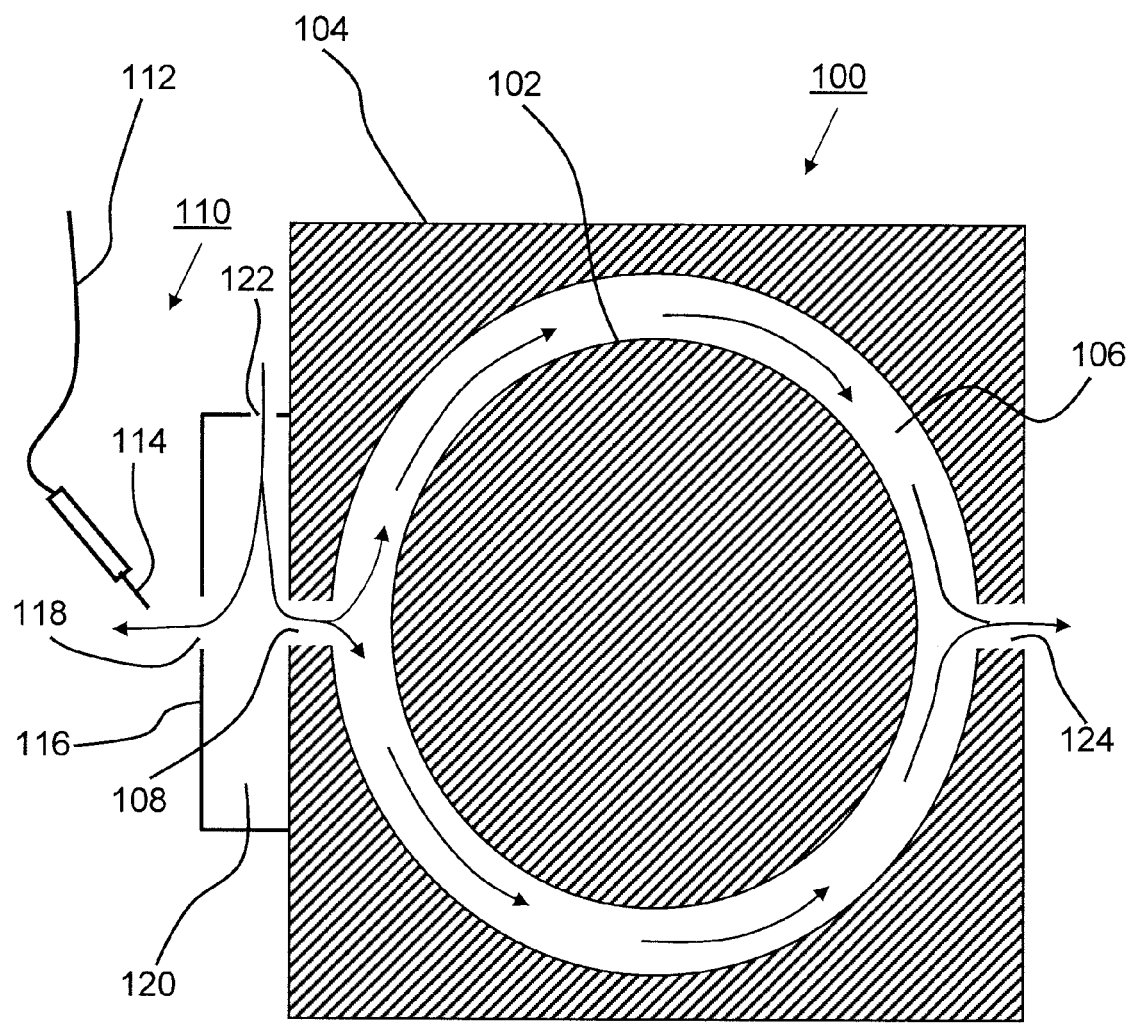
FIG. 1 is a simplified cross-sectional view showing a prior art side-to-side FAIMS apparatus.

Referring to FIG. 1, shown is a simplified cross-sectional view of a prior art side-to-side FAIMS apparatus including a separate chamber for desolvating electrosprayed ions. The side-to-side FAIMS apparatus, which is shown generally at 100, includes an analyzer region that is defined by first and second electrodes 102 and 104, respectively. The first electrode 102 is an inner electrode that is approximately circular in cross-section and that has a generally cylindrical outer surface. The second electrode 104 is an outer electrode that has a generally cylindrical inner surface facing the outer surface of the first electrode 102. An electrically insulating material (not shown) supports the first electrode 102 and the second electrode 104 in an overlapping, spaced-apart arrangement one relative to the other. An annular space between the outer surface of the first electrode 102 and the inner surface of the second electrode 104 defines an analytical gap 106 for separating ion species one from another. The analytical gap 106 is of approximately uniform width and extends around the circumference of the first electrode 102. The first electrode 102 is in electrical communication with a not illustrated power supply, which during use is capable of applying a high voltage asymmetric waveform (DV) and a low voltage dc compensation voltage (CV) to the first electrode 102.

An ion inlet orifice 108 is provided through the second electrode 104 for introducing ions from an ion source into the analytical gap 106. The ion source may take the form of an electrospray ionization ion source 110 including a liquid delivery capillary 112 and a fine-tipped electrospray needle 114 that is held at high voltage relative to an adjacent surface. The electrospray needle 114 is contained within a not illustrated electrospray ionization (ESI) chamber. Adjacent to the ionization source is a curtain plate 116 serving as a counter-electrode for the electrospray needle 114. An orifice 118 within the curtain plate electrode 116 allows for transmission of ions that are produced at the electrospray needle 114 into a separate desolvation chamber 120. A flow of a gas, which is represented in FIG. 1 by a series of closed-headed arrows, is provided through a gas inlet orifice 122 into the desolvation chamber 120. A first portion of the gas flows into the analytical gap 106 to carry the ions around the first electrode 102 and toward an ion outlet orifice 124. The orifice 118 that is defined within the curtain plate 116 allows for the flow of a second portion of the gas in a direction that is counter-current to the direction in which the ions are traveling within the desolvation chamber 120, so as to desolvate the ions before they are introduced into the analyzer region 106. The flow of the second portion of the gas exits the not illustrated ESI chamber via a gas outlet orifice thereof, thereby removing solvent vapor and minimizing the introduction of neutral species into the FAIMS analytical gap 106.

Once inside the analytical gap 106 of the FAIMS 100, the ions (not shown) are carried through an electric field that is formed by the application of the DV and the CV to the first electrode 102. Ion separation occurs within the FAIMS analytical gap 106 on the basis of the high field mobility properties of the ions. Those ions that have a stable trajectory for a particular combination of DV and CV are selectively transmitted through the FAIMS analytical gap 106, whilst other ions collide with an electrode surface and are lost. The selectively transmitted ions are extracted from the analytical gap 106 via the ion outlet orifice 124.

When the flow of gas that is introduced via the gas inlet orifice 122 is a 50:50 $He/N_2$ mixture, a substantial amount of He flows out through orifice 118 to desolvate the ions that are produced at the electrospray needle 114. For instance, assuming a total flow of 1 liter per minute through the gas inlet orifice 122 and equal splitting of the total flow between the first and second portions of the gas, it follows that 500 mL/min He is required, of which 250 ml/min is used to desolvate ions and the remaining 250 mL/min is used for ion transport within analytical gap 106. Using He gas, which is expensive compared to $N_2$ gas, for desolvating ions raises unnecessarily the operating cost of the FAIMS apparatus 100.

Figure 2A:
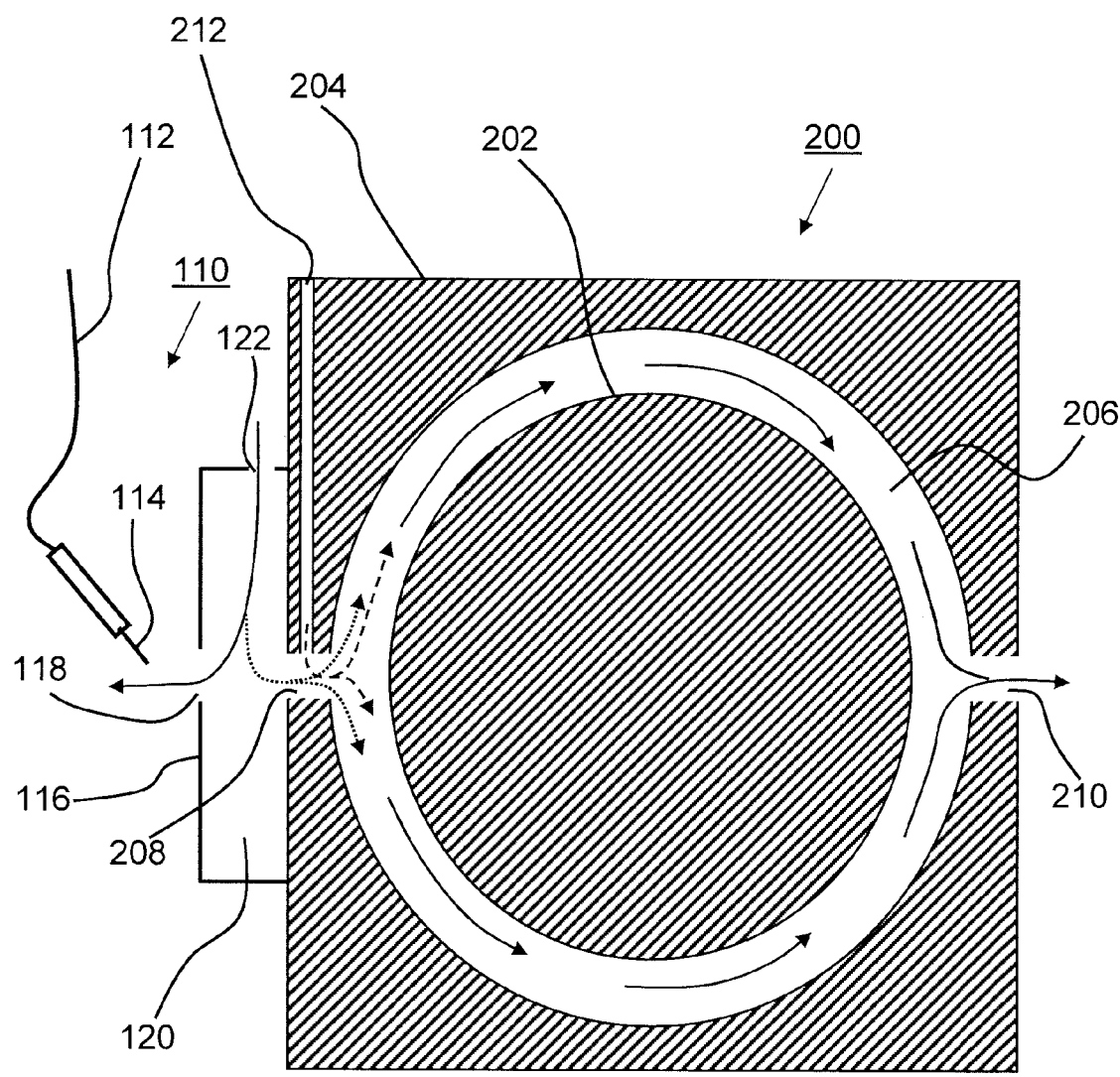
FIG. 2a is a simplified cross-sectional view showing a side-to-side FAIMS apparatus according to an embodiment of the instant invention.

Referring now to FIG. 2a, shown is a simplified cross-sectional view of a side-to-side FAIMS apparatus according to an embodiment of the instant invention. The side-to-side FAIMS apparatus, which is shown generally at 200, includes an analyzer region that is defined by first and second electrodes 202 and 204, respectively. The first electrode 202 is an inner electrode that is approximately circular in cross-section and that has a generally cylindrical outer surface. The second electrode 204 is an outer electrode having a generally cylindrical inner surface facing the outer surface of the first electrode 202. An electrically insulating material (not shown) supports the first electrode 202 and the second electrode 204 in an overlapping, spaced-apart arrangement one relative to the other. An annular space between the outer surface of the first electrode 202 and the inner surface of the second electrode 204 defines an analytical gap 206. The analytical gap 206 is of approximately uniform width and extends around the circumference of the first electrode 202. The first electrode 202 is in electrical communication with a not illustrated power supply, which during use is capable of applying a high voltage asymmetric waveform (DV) and a low voltage dc compensation voltage (CV) to the first electrode 202.

An ion inlet orifice 208 is provided through the second electrode 204 for introducing ions from an ion source into the analytical gap 206. The ion source may take the form of an electrospray ionization ion source 110 including a liquid delivery capillary 112 and a fine-tipped electrospray needle 114 that is held at high voltage relative to an adjacent surface. The electrospray needle 114 is contained within a not illustrated electrospray ionization (ESI) chamber. Adjacent to the ionization source is a curtain plate 116 serving as a counter-electrode for the electrospray needle 114. An orifice 118 within the curtain plate electrode 116 allows for transmission of ions that are produced at the electrospray needle 114 into a separate desolvation chamber 120. A flow of a desolvation gas is provided through gas inlet orifice 122 into the desolvation chamber 120, via a not illustrated gas conduit that is in communication with a desolvation gas source. A first portion of the desolvation gas, which is denoted in FIG. 2a using dotted lines, enters the analytical gap 206 and passes out through ion outlet orifice 210.

Referring still to FIG. 2a, the orifice 118 within the curtain plate 116 allows a second portion of the desolvation gas, which is denoted in FIG. 2a using a solid line, to travel in a direction that is counter-current to the direction in which the ions are moving within the desolvation chamber 120, so as to desolvate the ions before they are introduced into the analytical gap 206. The second portion of the desolvation gas exits the not illustrated ESI chamber via a gas outlet orifice thereof, thereby removing solvent vapor and minimizing the introduction of neutral species into the FAIMS analytical gap 206. By way of a specific and non-limiting example, the desolvation gas that is provided into the desolvation chamber 120 via the gas inlet orifice 122 is substantially nitrogen gas ($N_2$).

A separate gas conduit 212 is provided through a portion of the second electrode 204 and opening into the ion inlet orifice 208. A flow of a carrier gas is provided via the carrier gas conduit 212 directly into the ion inlet orifice, as denoted using the dashed lines in FIG. 2a. By way of a specific and non-limiting example, an end of the gas conduit 212 that is opposite the ion inlet orifice end is in fluid communication with a source of helium gas (He). By adjusting the relative flow rates of the $N_2$ gas and of the He gas, the He gas exiting from the gas conduit 212 is directed preferentially into the analytical gap 206 where it mixes with the first portion of the desolvation gas, thereby forming a mixed gas flow within the analytical gap 206. During use, the mixed gas flow transports the not illustrated ions through an electric field that is formed within the analytical gap 206 by the application of the DV and the CV to the first electrode 202. Ion separation occurs within the analytical gap 206 on the basis of the high field mobility properties of the ions. Those ions that have a stable trajectory for a particular combination of DV and CV are selectively transmitted through the analytical gap 206, whilst other ions collide with an electrode surface and are lost. The selectively transmitted ions are extracted from the analytical gap 206 via the ion outlet orifice 210.

In FIG. 2a, ions that are produced at the electrospray needle 114 are caused to travel downstream along an ion flow path through the desolvation chamber 120, into analytical gap 206 and eventually out through ion outlet orifice 210. The gas conduit 212 provides a flow of carrier gas, such as for instance He, via an outlet end thereof that is open adjacent to a portion of the ion flow path that is defined downstream relative to the desolvation chamber. In the specific example that is shown in FIG. 2a, the portion of the ion flow path that is defined downstream relative to the desolvation chamber is within the ion inlet orifice 208. Assuming that the He gas exiting the gas conduit 212 is preferentially directed into the analytical gap 206, a total flow of only 250 mL/min He is required during operation of the FAIMS apparatus 200. By adjusting the flow of $N_2$ desolvation gas being introduced into the desolvation chamber 120 via gas inlet orifice 122, a total flow of 500 mL 50:50 He:$N_2$ still is achievable through the analytical gap. Advantageously, a flow of relatively inexpensive $N_2$ gas is used to desolvate the ions that are produced at electrospray needle 114. Of course, the numerical values that are provided in this example are intended to be illustrative in nature. The actual He gas savings depend on many characteristics of the FAIMS apparatus 200 being considered relative to the prior art FAIMS apparatus 100.

Figure 2B:
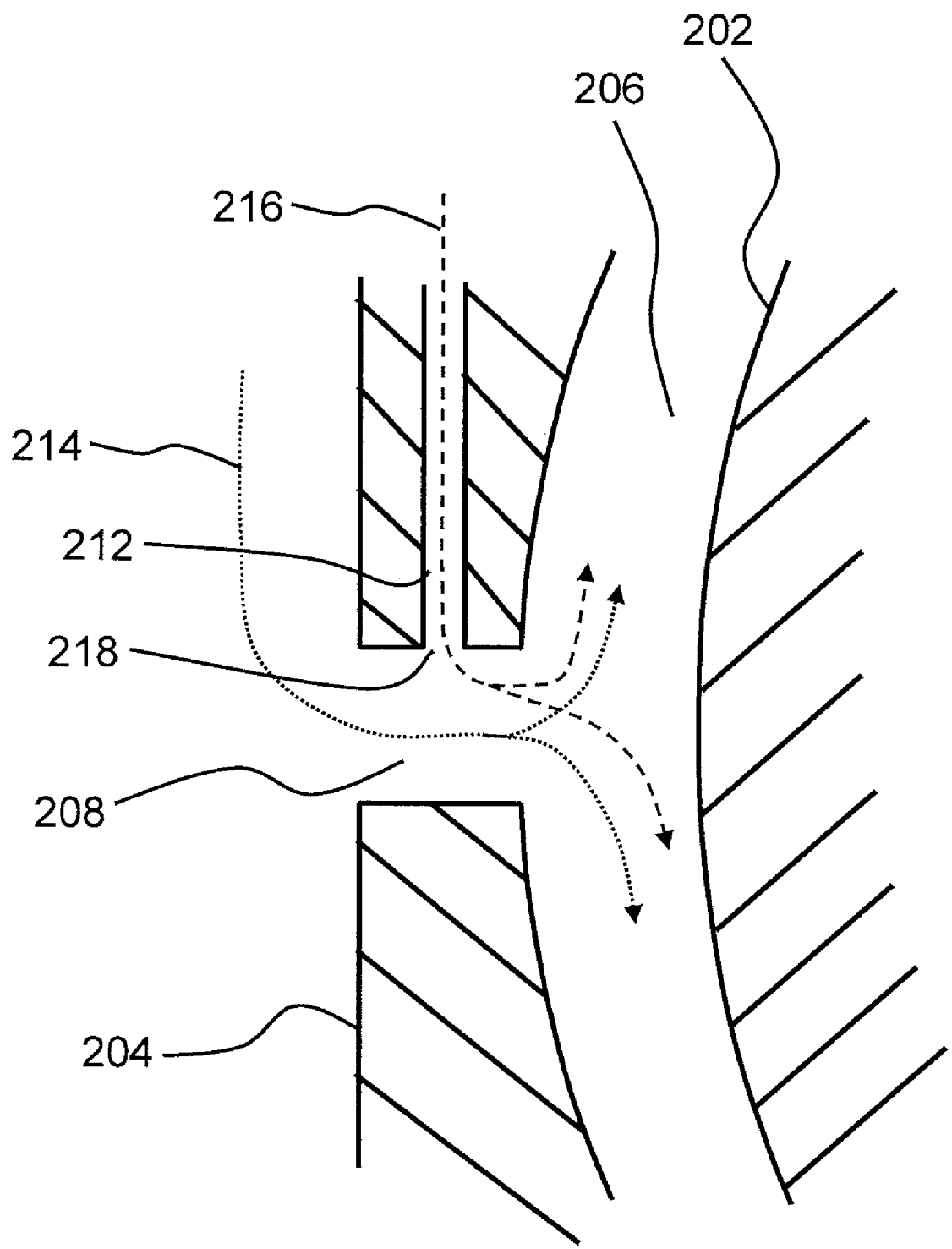

Referring now to FIG. 2b, shown is an enlarged view of the ion inlet configuration of the FAIMS apparatus of FIG. 2a. The gas conduit 212 extends through a portion of the second electrode 204. By way of a specific and non-limiting example, the gas conduit 212 is formed by boring through the portion of the second electrode 204 and out through the sidewall surface of the ion inlet orifice 208. In this way, a carrier gas inlet orifice 218 is defined within the sidewall surface of the ion inlet orifice 208. In the instant example, the gas conduit 212 is substantially linear and is also substantially parallel to the outer surface of the second electrode 204. More particularly, a longitudinal axis extending along the gas conduit 212 is substantially normal to the sidewall surface of the ion inlet orifice 208. In the embodiment that is shown in FIG. 2b, the gas conduit 212 does not direct a flow of carrier gas preferentially toward the analytical gap 206.

Figure 2C:
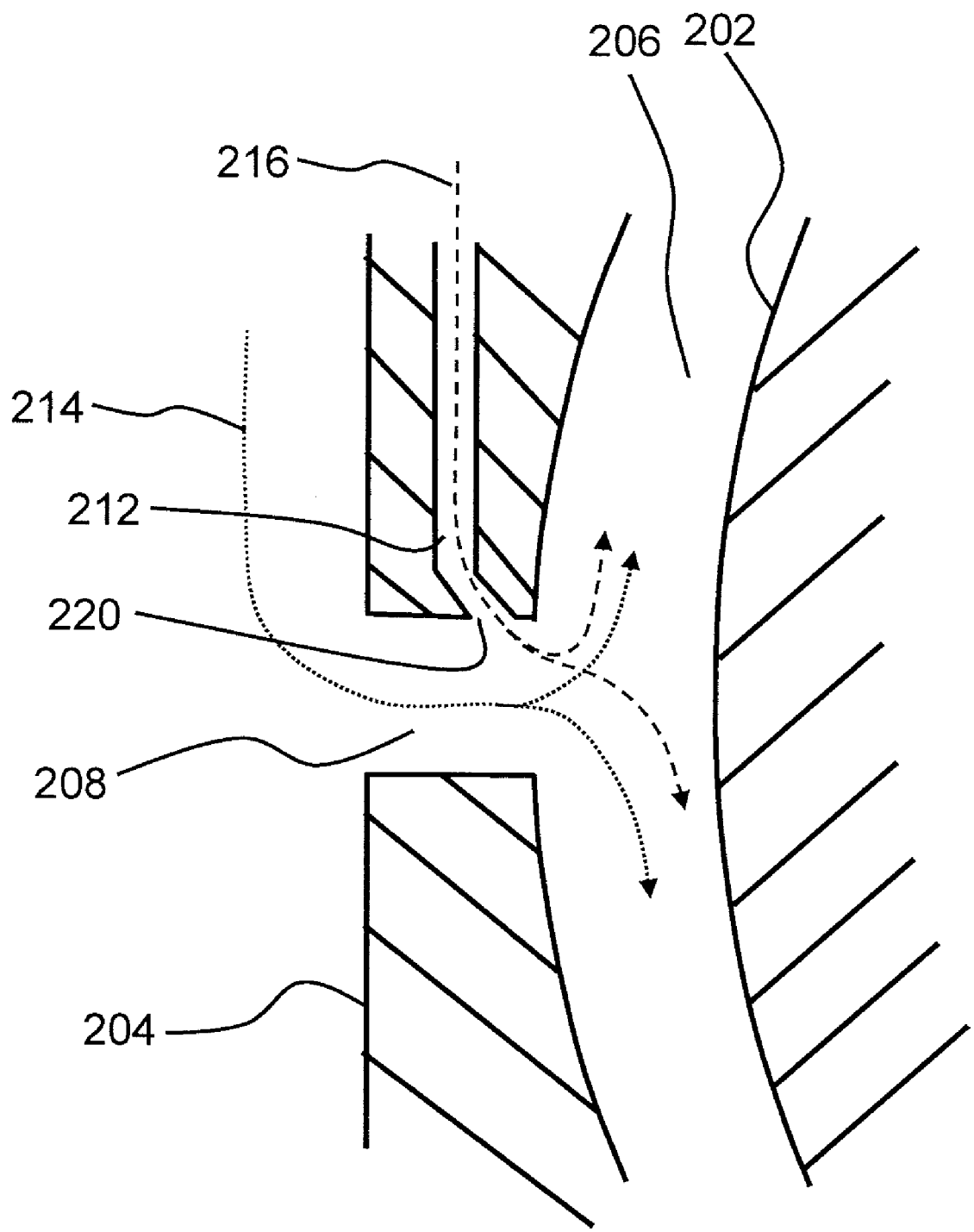

Referring now to FIG. 2c, shown is an enlarged view of a first alternative ion inlet configuration of the FAIMS apparatus of FIG. 2a. The gas conduit 212 is shown with an angled outlet end defining a carrier gas inlet orifice 220 within the sidewall surface of the ion inlet orifice 208. In particular, the outlet end is angled with respect to the remainder of the gas conduit 212, such that the gas conduit 212 directs a flow of carrier gas preferentially toward the analytical gap 206 and away from the desolvation chamber 120.

Figure 2D:
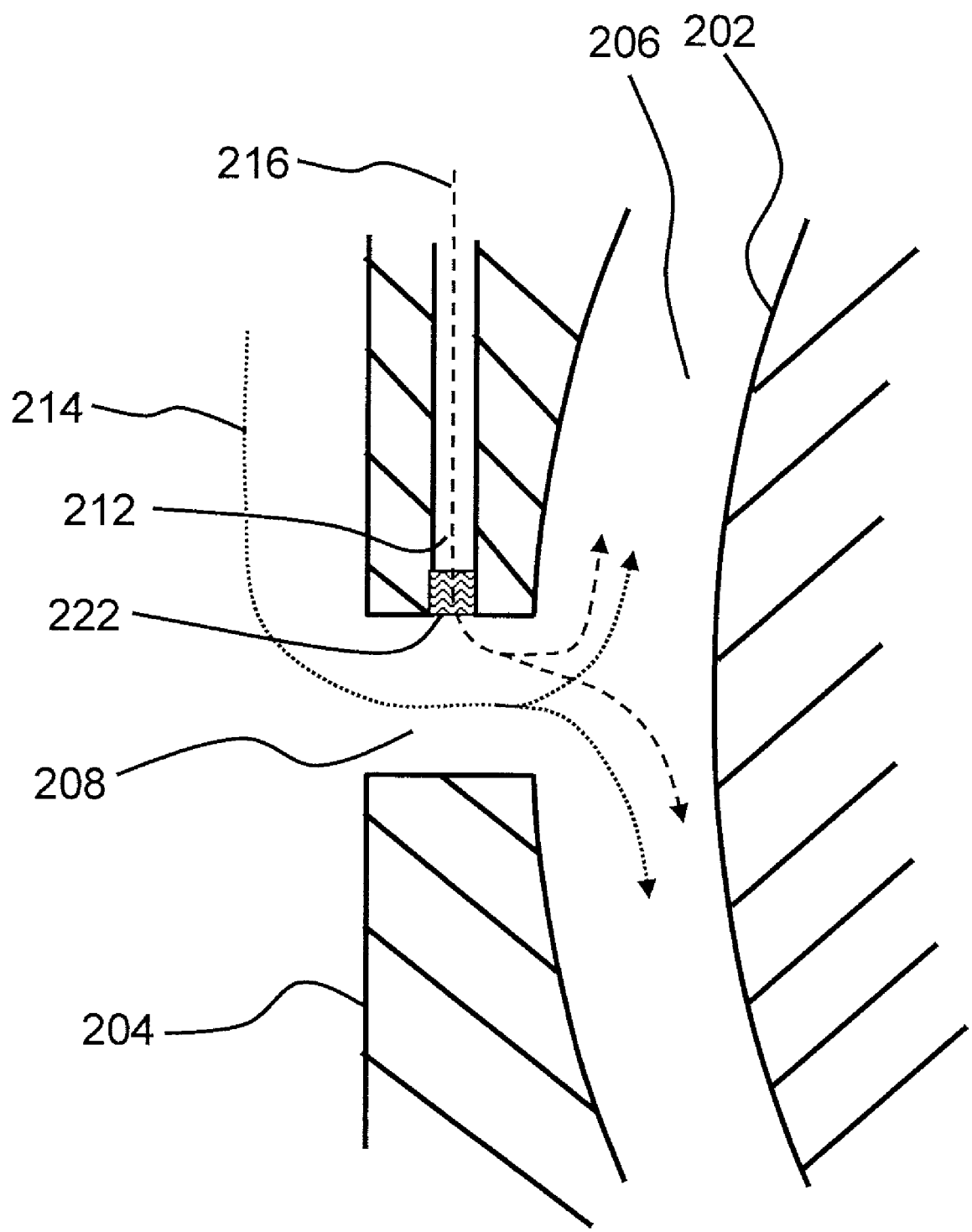

Referring now to FIG. 2d, shown is an enlarged view of a second alternative ion inlet configuration of the FAIMS apparatus of FIG. 2a. The gas conduit 212 is shown with an outlet end 218 thereof defining an opening within the sidewall surface of the ion inlet orifice 208, within which opening is disposed a gas-distributing element 222. In FIG. 2d the outlet end 218 is substantially collinear with the remainder of the gas conduit 212 and is substantially normal to the sidewall surface of the ion inlet orifice 208. By way of a specific and non-limiting example, the gas-distributing element 222 is provided in the form of a plug of a porous material, through which the carrier gas is made to flow. Optionally, another type of gas-distributing element, such as for instance a tunable flow-element or an adjustable-orientation fin is provided for controlling and/or directing the flow of carrier gas.

Figure 3A:
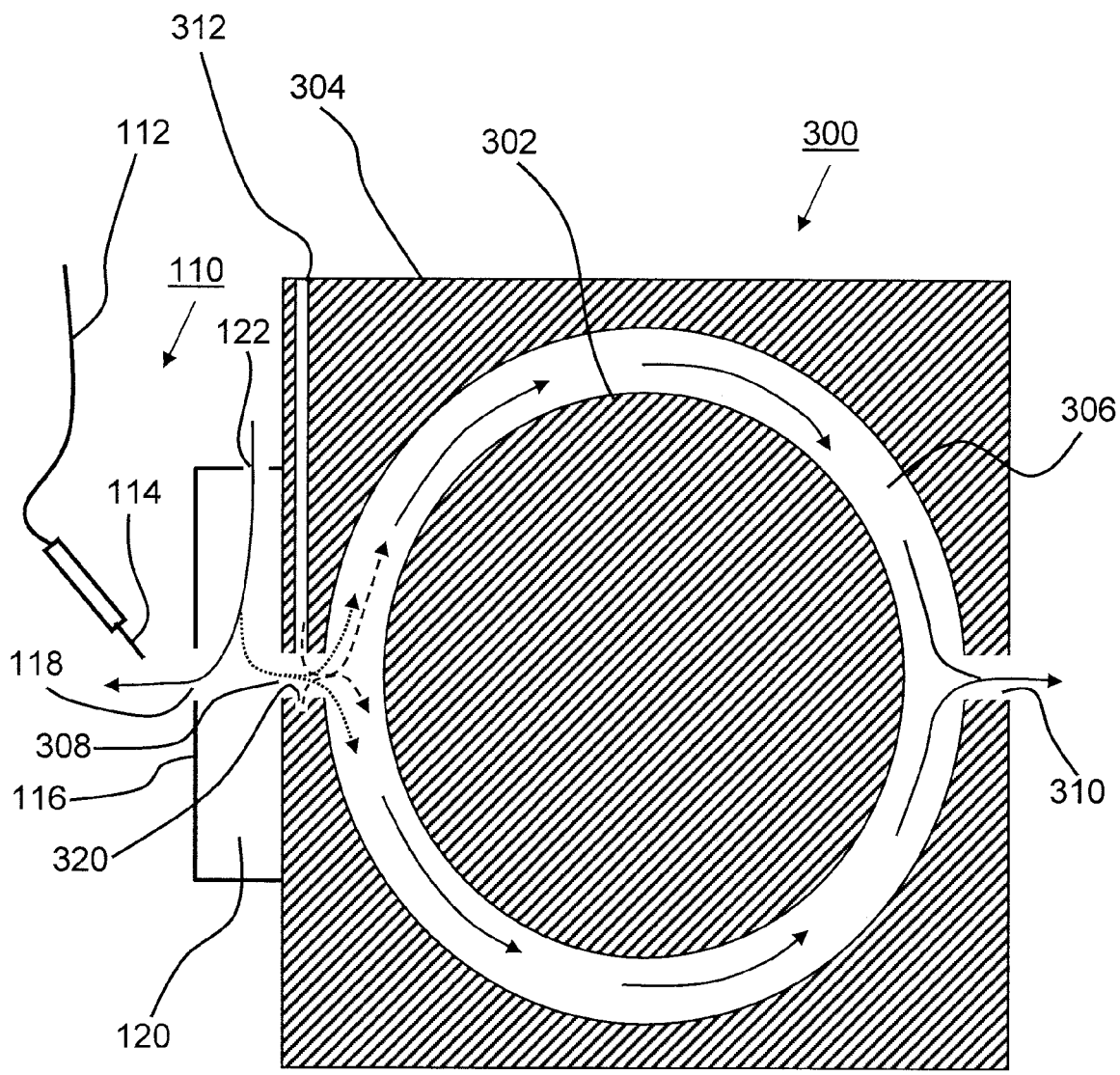
FIG. 3a is a simplified cross-sectional view showing a side-to-side FAIMS apparatus according to an embodiment of the instant invention.

Referring now to FIG. 3a, shown is a simplified cross-sectional view of a side-to-side FAIMS apparatus according to an embodiment of the instant invention. The side-to-side FAIMS apparatus, which is shown generally at 300, includes an analyzer region that is defined by first and second electrodes 302 and 304, respectively. The first electrode 302 in an inner electrode that is approximately circular in cross-section and has a generally cylindrical outer surface. The second electrode 304 is an outer electrode having a generally cylindrical inner surface facing the outer surface of the first electrode 302. An electrically insulating material (not shown) supports the first electrode 302 and the second electrode 304 in an overlapping, spaced-apart arrangement one relative to the other. An annular space between the outer surface of the first electrode 302 and the inner surface of the second electrode 304 defines an analytical 306. The analytical gap 306 is of approximately uniform width and extends around the circumference of the first electrode 302. The first electrode 302 is in electrical communication with a not illustrated power supply, which during use is capable of applying a high voltage asymmetric waveform (DV) and a low voltage dc compensation voltage (CV) to the first electrode 302.

An ion inlet orifice 308 is provided through the second electrode 304 for introducing ions from an ion source into the analytical gap 306. The ion source may take the form of an electrospray ionization ion source 110 including a liquid delivery capillary 112 and a fine-tipped electrospray needle 114 that is held at high voltage relative to an adjacent surface. The electrospray needle 114 is contained within a not illustrated electrospray ionization (ESI) chamber. Adjacent to the ionization source is a curtain plate 116 serving as a counter-electrode for the electrospray needle 114. An orifice 118 within the curtain plate electrode 116 allows for transmission of ions that are produced at the electrospray needle 114 into a separate desolvation chamber 120. A flow of a desolvation gas is provided through gas inlet orifice 122 into the desolvation chamber 120 via a not illustrated gas conduit that is in communication with a desolvation gas source. A first portion of the desolvation gas, which is denoted in FIG. 3a using dotted lines, enters the analytical gap 306 and passes out through ion outlet orifice 310.

Referring still to FIG. 3a, the orifice 118 within the curtain plate 116 allows a second portion of the desolvation gas, which is denoted in FIG. 3a using a solid line, to travel in a direction that is counter-current to the direction in which the ions are moving within the desolvation chamber 120, so as to desolvate the ions before they are introduced into the analytical gap 306. The second portion of the desolvation gas exits the not illustrated ESI chamber via a gas outlet orifice thereof, thereby removing solvent vapor and minimizing the introduction of neutral species into the analytical gap 306. By way of a specific and non-limiting example, the desolvation gas that is provided into the desolvation chamber 120 via the gas inlet orifice 122 is substantially nitrogen gas ($N_2$).

A separate gas conduit 312 is provided through a portion of the second electrode 304 and opening into the ion inlet orifice 308. More specifically, the gas conduit 312 is in fluid communication with the ion inlet orifice 308 via a circumferential ring-shaped channel 320 that is defined within the sidewall surface of the ion inlet orifice 308. A flow of a carrier gas is provided via the gas conduit 312 and into the ring-shaped channel 320, as denoted using the dashed lines in FIG. 3a. In particular, a plurality of flows of the carrier gas is provided into the ion inlet orifice 308 and then into the FAIMS analytical gap 306. By way of a specific and non-limiting example, an end of the gas conduit 312 that is opposite the ion inlet orifice end is in fluid communication with a source of helium gas (He). By adjusting the relative flow rates of the $N_2$ gas and of the He gas, the He gas exiting from the gas conduit 312 is directed preferentially into the analytical gap 306 where it mixes with the first portion of the desolvation gas, thereby forming a mixed carrier gas flow within the analytical gap 306. During use, the mixed carrier gas flow transports the not illustrated ions through an electric field that is formed within the analytical gap 306 by the application of the DV and the CV to the first electrode 302. Ion separation occurs within the analytical gap 306 on the basis of the high field mobility properties of the ions. Those ions that have a stable trajectory for a particular combination of DV and CV are selectively transmitted through the analytical gap 306, whilst other ions collide with an electrode surface and are lost. The selectively transmitted ions are extracted from the analyzer region 306 via the ion outlet orifice 310.

In FIG. 3a, ions that are produced at the electrospray needle 114 are caused to travel downstream along an ion flow path through the desolvation chamber 120, into analytical gap 306 and eventually out through ion outlet orifice 310. The gas conduit 312 provides a flow of carrier gas, such as for instance He, via an outlet end thereof that is open adjacent to a portion of the ion flow path that is defined downstream relative to the desolvation chamber 120. In the specific example that is shown in FIG. 3a, the portion of the ion flow path that is defined downstream relative to the desolvation chamber is within the ion inlet orifice 308. Assuming that the He gas exiting the gas conduit 312 is preferentially directed into the analytical gap 306, a total flow of only 250 mL/min He is required during operation of the FAIMS apparatus 300. By adjusting the flow of $N_2$ desolvation gas being introduced into the desolvation chamber 120 via gas inlet orifice 122, a total flow of 500 mL 50:50 He:$N_2$ still is achievable through the analytical gap. Advantageously, a flow of relatively inexpensive $N_2$ gas is used to desolvate the ions that are produced at electrospray needle 114. Of course, the numerical values that are provided in this example are intended to be illustrative in nature. The actual He gas savings depend on many characteristics of the FAIMS apparatus 300 being considered relative to the prior art FAIMS apparatus 100.

Figure 3B:
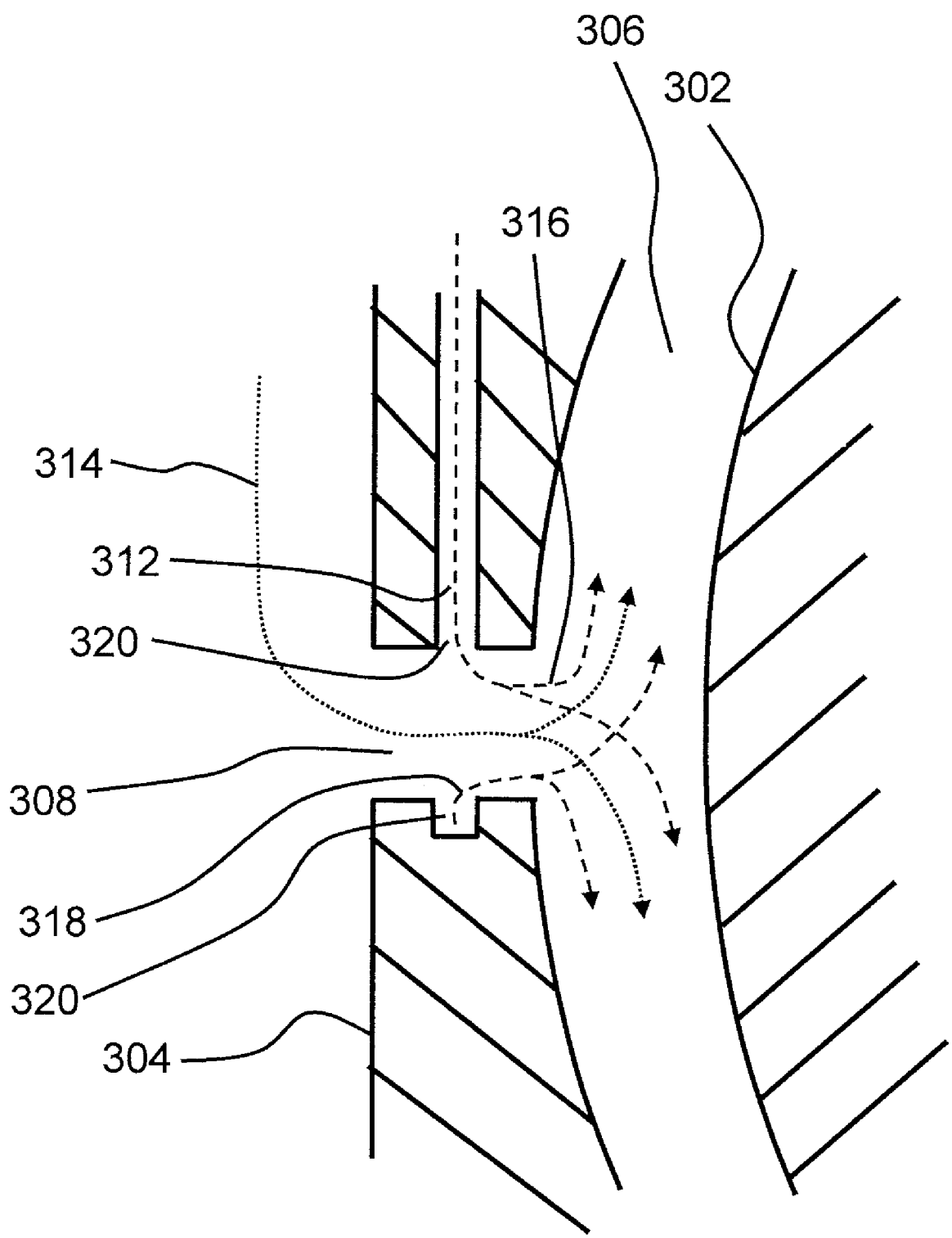

Referring now to FIG. 3b, shown is an enlarged view of the ion inlet configuration of the FAIMS apparatus of FIG. 3a. The gas conduit 312 extends through a portion of the second electrode 304. By way of a specific and non-limiting example, the gas conduit 312 is formed by boring through the portion of the second electrode 304 and out through the ring-shaped channel 320 that is recessed within the sidewall surface of the ion inlet orifice 308.

Figure 3C:
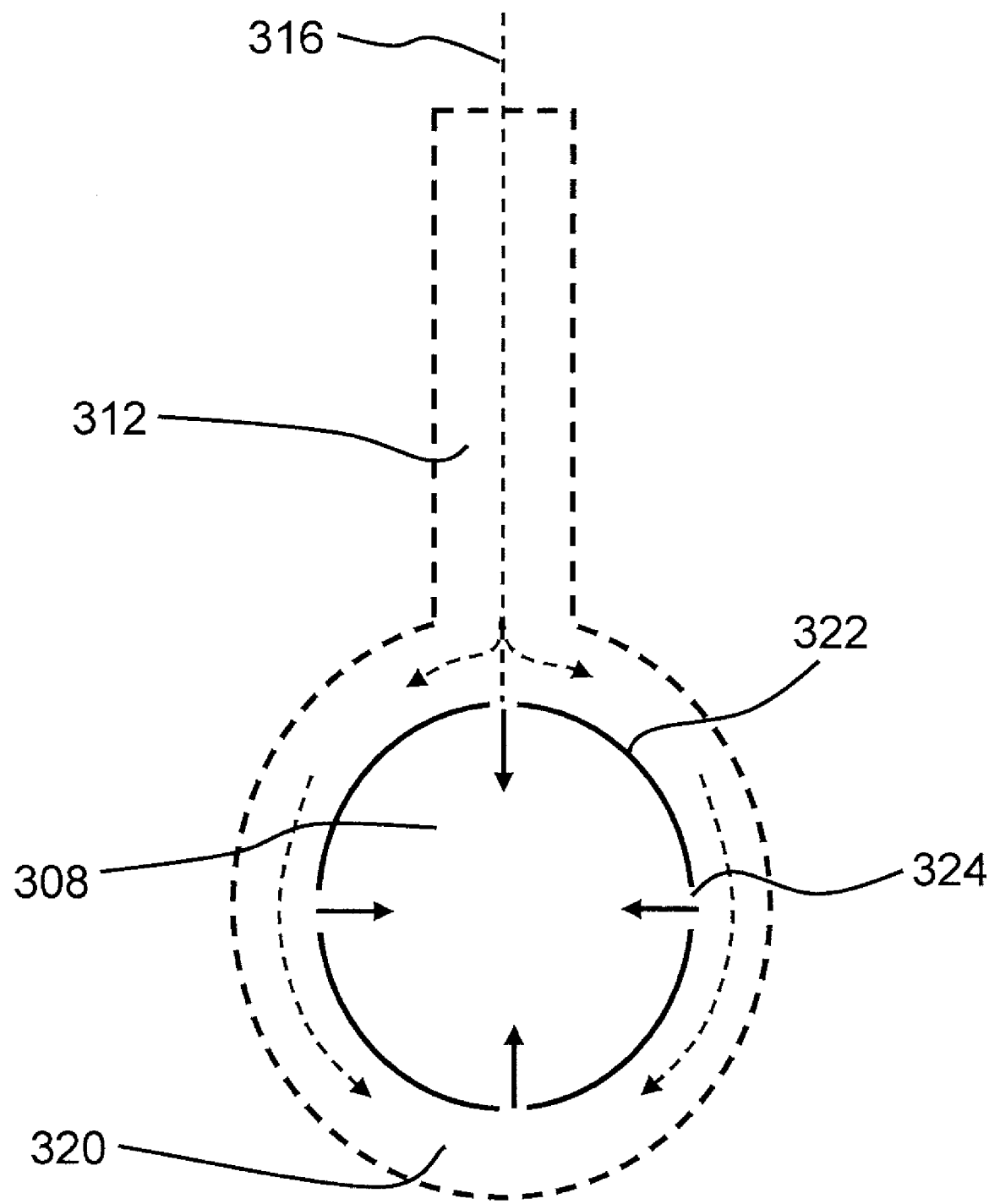
FIG. 3c is a simplified top view of the ion inlet configuration of FIG. 3b.

Referring now to FIG. 3c, shown is a simplified top view of the ion inlet configuration of FIG. 3b. A barrier material 322 is disposed within the ring-shaped channel 320 for directing the flow of gas around the ring-shaped channel and out through a plurality of openings 324, which openings are circumferentially spaced around the ion inlet orifice 308. In the instant example, four discrete openings 324 are shown for radially directing four separate flows of the gas into the ion inlet orifice 308.

Figure 3D:
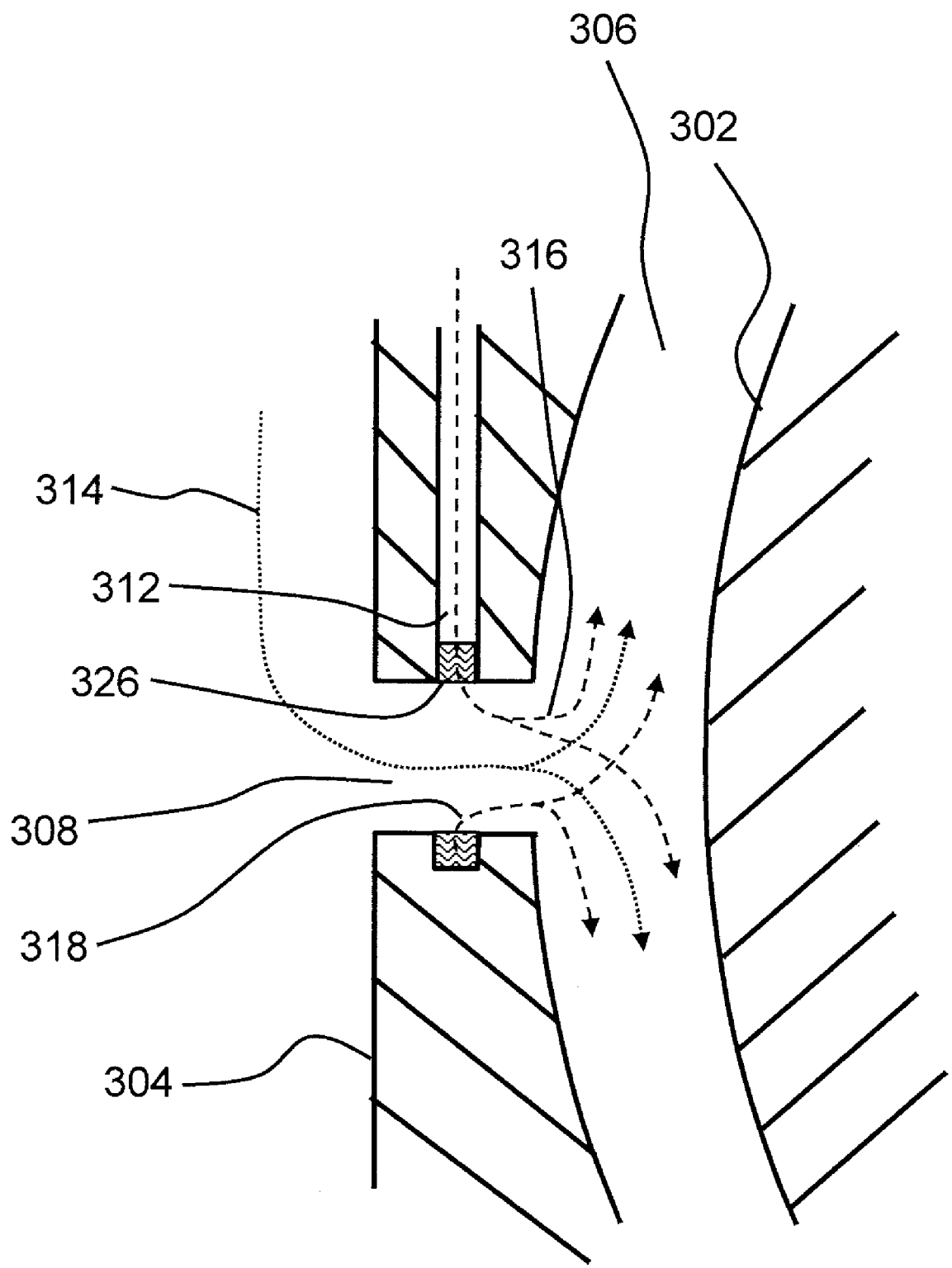

Referring now to FIG. 3d, shown is an enlarged view of an alternative ion inlet configuration of the FAIMS apparatus of FIG. 3a. The gas conduit 312 extends through a portion of the second electrode 304. By way of a specific and non-limiting example, the gas conduit 312 is formed by boring through the portion of the outer electrode 304 and out through the ring-shaped channel 320 that is recessed within the sidewall surface of the ion inlet orifice 308. Disposed within the ring-shaped channel 320 is a gas-distributing element 226. By way of a specific and non-limiting example, the gas-distributing element 322 is provided in the form of a plug of a porous material through which the carrier gas is made to flow. The plug is ring-shaped so as to fit within the ring-shaped channel 320 and be substantially flush with the sidewall surface of the ion inlet orifice 308. Gas flows out of the gas-distributing element 322 and into the ion inlet orifice 308 around the circumference thereof.

Figure 3E:
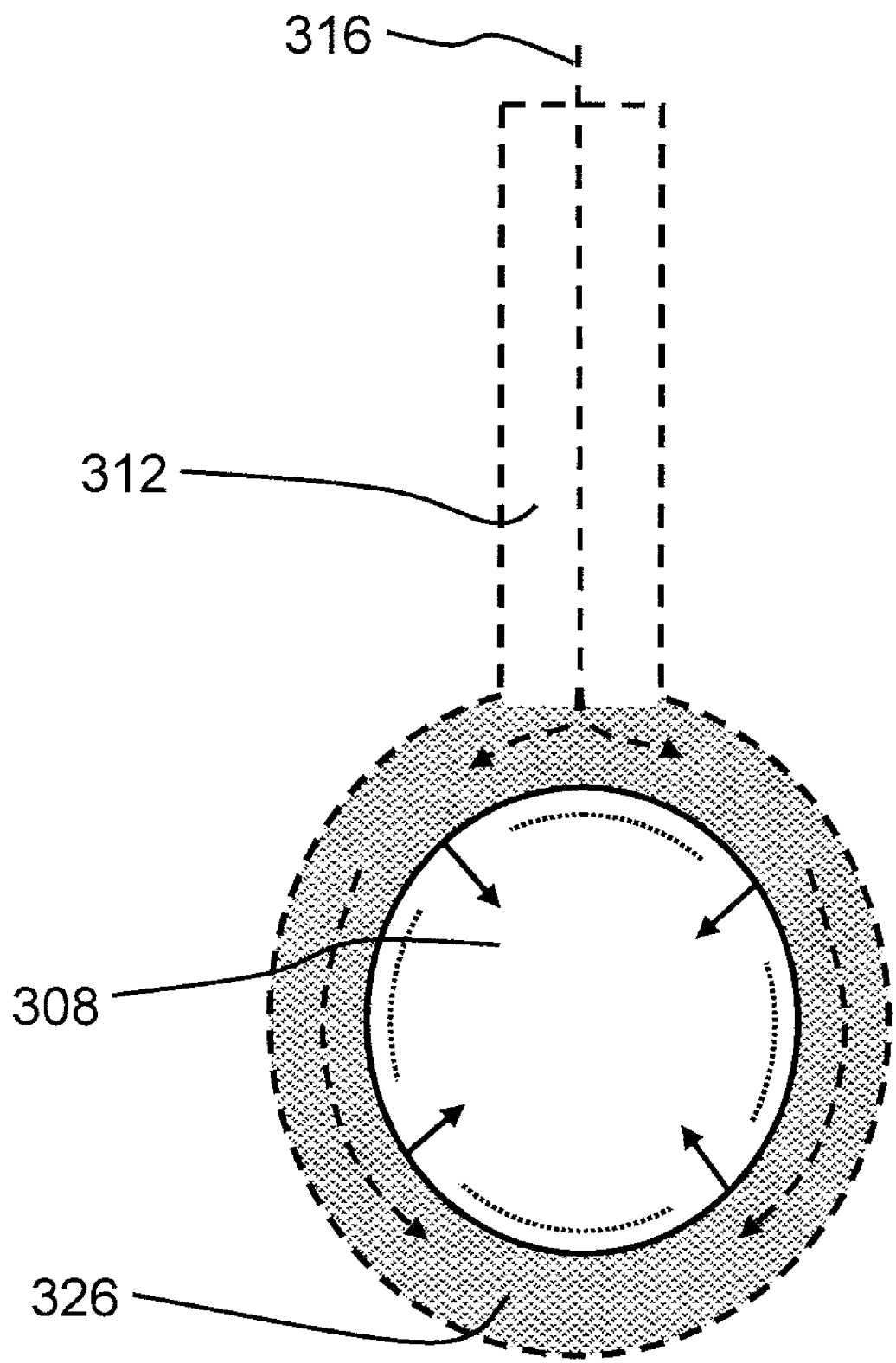
FIG. 3e is a simplified top view of the ion inlet configuration of FIG. 3d.

Referring now to FIG. 3e, shown is a simplified top view of the ion inlet configuration of FIG. 3d. Notably, the ring-shaped gas-distributing element 326 is shown disposed within the recessed channel 320 and flush mounted relative to the sidewall surface of the ion inlet orifice 308. The dotted arc-lines within the ion inlet orifice 308 indicate that gas flows out of the gas-distributing element 326 around substantially the entire circumference of the gas-distributing element 326.

Figure 4A:
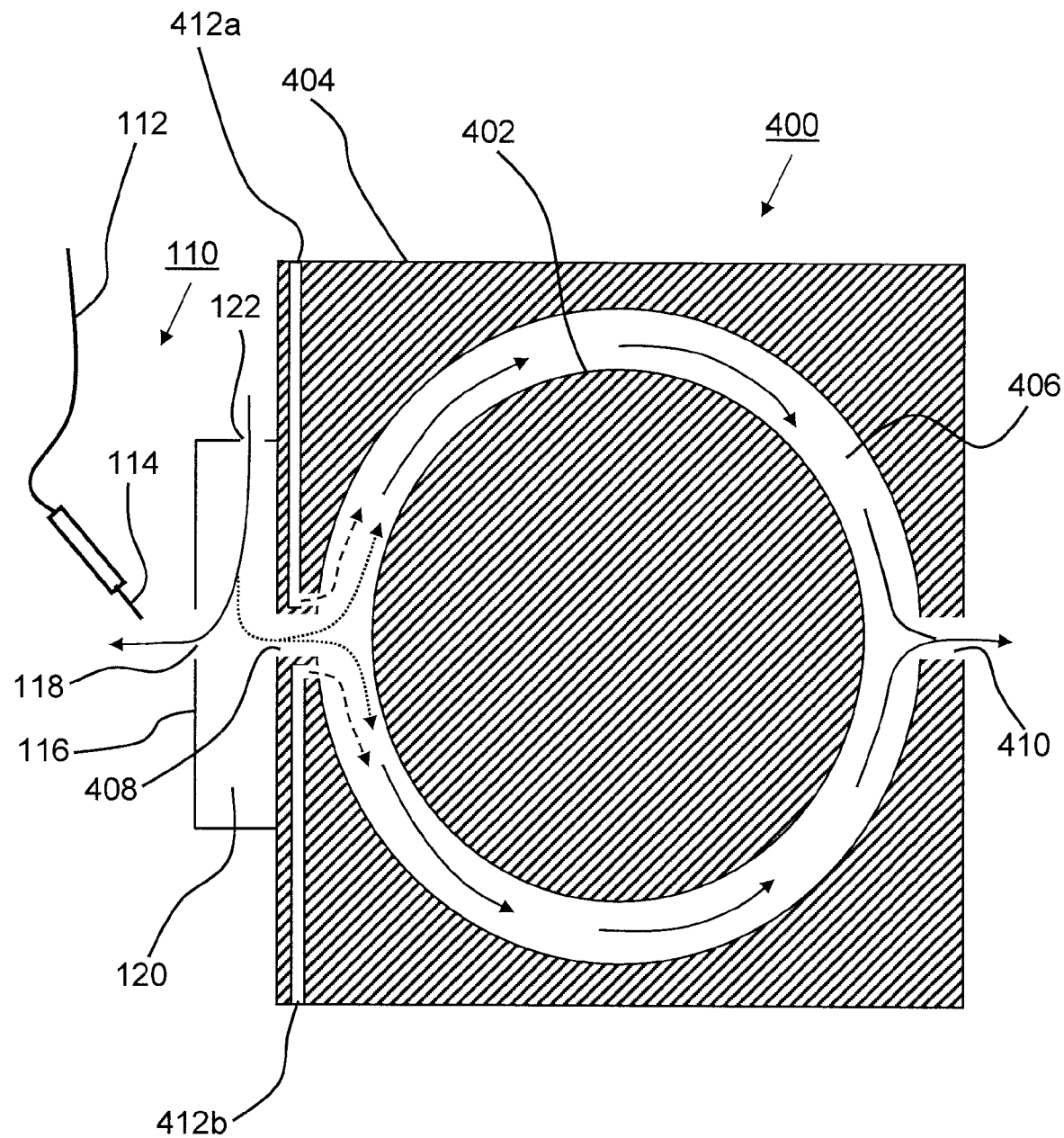
FIG. 4a is a simplified cross-sectional view showing a side-to-side FAIMS apparatus according to an embodiment of the instant invention.

Referring now to FIG. 4a, shown is a simplified cross-sectional view of a side-to-side FAIMS apparatus according to an embodiment of the instant invention. The side-to-side FAIMS apparatus, which is shown generally at 400, includes an analyzer region that is defined by first and second electrodes 402 and 404, respectively. The first electrode 402 is an inner electrode that is approximately circular in cross-section and that has a generally cylindrical outer surface. The second electrode 404 is an outer electrode having a generally cylindrical inner surface facing the outer surface of the first electrode 402. An electrically insulating material (not shown) supports the first electrode 402 and the second electrode 404 in an overlapping, spaced-apart arrangement one relative to the other. An annular space between the outer surface of the first electrode 402 and the inner surface of the second electrode 404 defines an analytical gap 406. The analytical gap 406 is of approximately uniform width and extends around the circumference of the first electrode 402. The first electrode 402 is in electrical communication with a not illustrated power supply, which during use is capable of applying a high voltage asymmetric waveform (DV) and a low voltage dc compensation voltage (CV) to the first electrode 402.

An ion inlet orifice 408 is provided through the second electrode 404 for introducing ions from an ion source into the analytical gap 406. The ion source may take the form of an electrospray ionization ion source 110 including a liquid delivery capillary 112 and a fine-tipped electrospray needle 114 that is held at high voltage relative to an adjacent surface. The electrospray needle 114 is contained within a not illustrated electrospray ionization (ESI) chamber. Adjacent to the ionization source is a curtain plate 116 serving as a counter-electrode for the electrospray needle 114. An orifice 118 within the curtain plate electrode 116 allows for transmission of ions that are produced at the electrospray needle 114 into a separate desolvation chamber 120. A flow of a desolvation gas is provided through gas inlet orifice 122 into the desolvation chamber 120, via a not illustrated gas conduit that is in communication with a desolvation gas source. A first portion of the desolvation gas, which is denoted in FIG. 4a using dotted lines, enters the analytical gap 406 and passes out through ion outlet orifice 410.

Referring still to FIG. 4a, the orifice 118 within the curtain plate 116 allows a second portion of the desolvation gas, which is denoted in FIG. 4a using a solid line, to travel in a direction that is counter-current to the direction in which the ions are moving within the desolvation chamber 120, so as to desolvate the ions before they are introduced into the analytical gap 406. The second portion of the desolvation gas exits the not illustrated ESI chamber via a gas outlet orifice thereof, thereby removing solvent vapor and minimizing the introduction of neutral species into the analytical gap 406. By way of a specific and non-limiting example, the desolvation gas that is provided into the desolvation chamber 120 via the gas inlet orifice 122 is substantially nitrogen gas ($N_2$).

Two separate gas conduits 412a and 412b are provided through portions of the second electrode 404 and opening directly into the ion analytical gap 406. Separate flows of a carrier gas are provided via the carrier gas conduits 412a and 412b directly into the analytical gap 406, as denoted using the dashed lines in FIG. 4a. By way of a specific and non-limiting example, an end of the carrier gas conduits 412a and 412b that is opposite the analytical gap end is in fluid communication with a source of helium gas (He). The He gas exiting from the gas conduits 412a and 412b is directed preferentially into the analytical gap 406 where it mixes with the first portion of the desolvation gas from the desolvation chamber 120, thereby forming a mixed gas flow within the analytical gap 406. During use, the mixed gas flow transports the not illustrated ions through an electric field that is formed within the analytical gap 406 by the application of the DV and the CV to the first electrode 402. Ion separation occurs within the analytical gap 406 on the basis of the high field mobility properties of the ions. Those ions that have a stable trajectory for a particular combination of DV and CV are selectively transmitted through the analytical gap 406, whilst other ions collide with an electrode surface and are lost. The selectively transmitted ions are extracted from the analytical gap 406 via the ion outlet orifice 410.

In FIG. 4a, ions that are produced at the electrospray needle 114 are caused to travel downstream along an ion flow path through the desolvation chamber 120, into analytical gap 406 and eventually out through ion outlet orifice 410. The gas conduits 412a and 412b provide flows of carrier gas, such as for instance He, via outlet ends thereof that are open adjacent to a portion of the ion flow path that is defined downstream relative to the desolvation chamber 120. In the specific example that is shown in FIG. 4a, the portion of the ion flow path that is defined downstream relative to the desolvation chamber is within the analytical gap 406. Accordingly, a total flow of only 250 mL/min He is required during operation of the FAIMS apparatus 400. By adjusting the flow of $N_2$ desolvation gas being introduced into the desolvation chamber 120 via gas inlet orifice 122, a total flow of 500 mL 50:50 He:$N_2$ still is achievable through the analytical gap 406. Advantageously, a flow of relatively inexpensive $N_2$ gas is used to desolvate the ions that are produced at electrospray needle 114. Of course, the numerical values that are provided in this example are intended to be illustrative in nature. The actual He gas savings depend on many characteristics of the FAIMS apparatus 400 being considered relative to the prior art FAIMS apparatus 100.

Figure 4B:
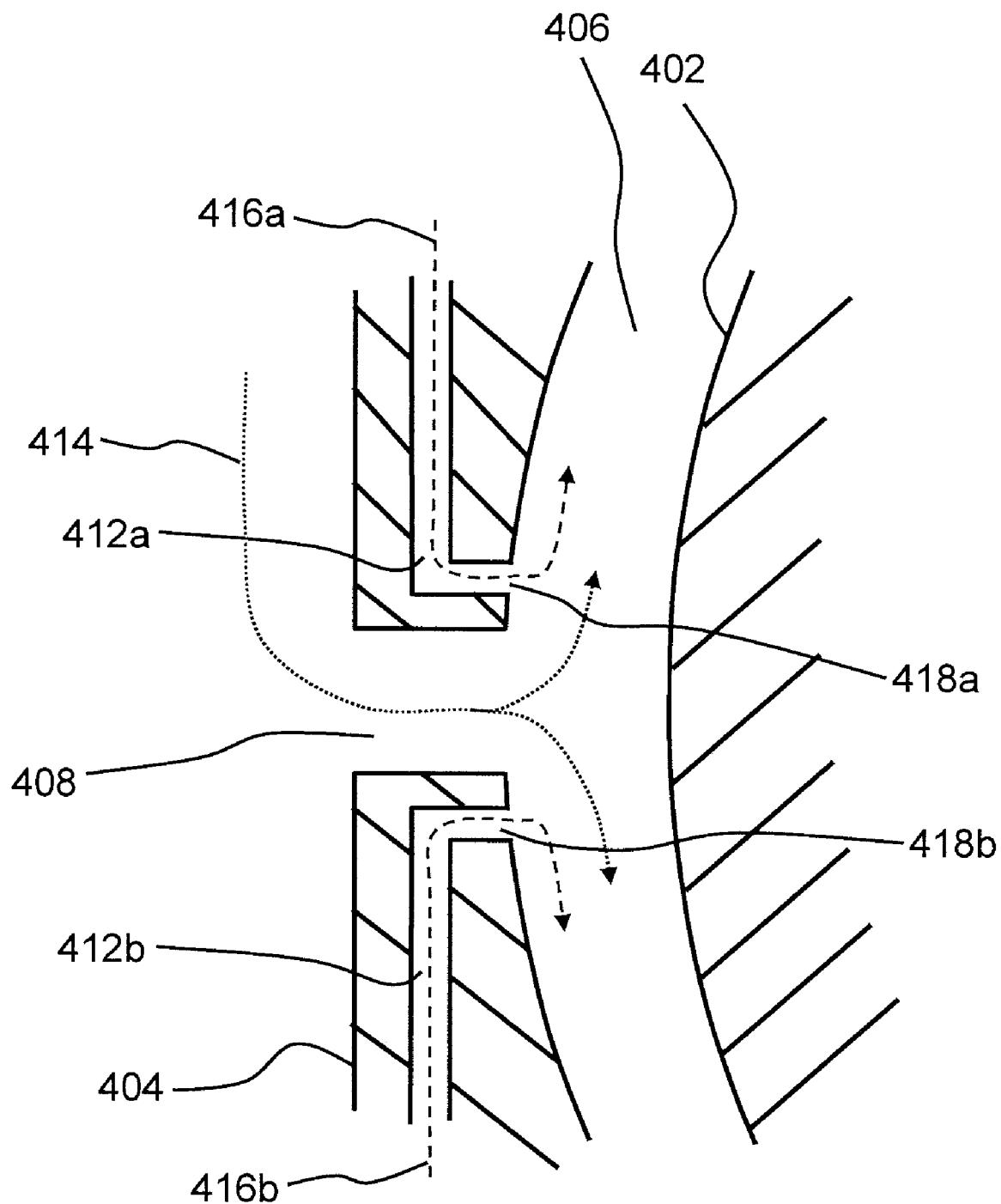

Referring now to FIG. 4b, shown is an enlarged view of the ion inlet configuration of the FAIMS apparatus of FIG. 4a. The gas conduits 412a and 412b each extend through a portion of the second electrode 404. In the instant example, the gas conduits 412a and 412b are shaped so as to open directly into the analytical gap 406 through the inner surface of second electrode 404. In the embodiment that is shown in FIG. 4b, the gas conduits 412a and 412b each provide a flow of the carrier gas directly into the analytical gap 406 where it mixes with the desolvation gas that is entering via the ion inlet orifice 408.

Figure 5:
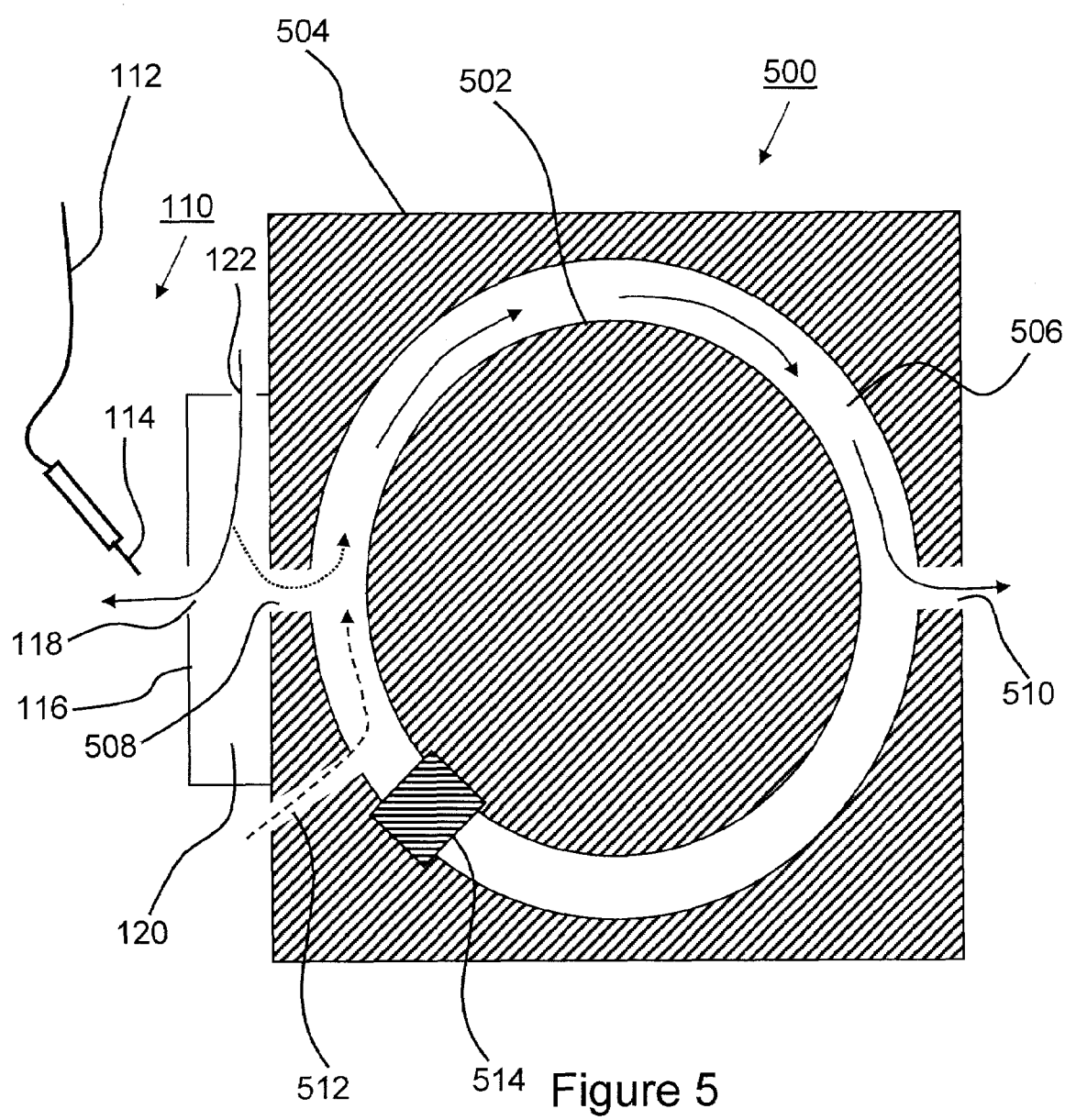
FIG. 5 is a simplified cross-sectional view showing a side-to-side FAIMS apparatus according to an embodiment of the instant invention.

Referring now to FIG. 5, shown is a simplified cross-sectional view of a side-to-side FAIMS apparatus according to an embodiment of the instant invention. The side-to-side FAIMS apparatus, which is shown generally at 500, includes an analyzer region that is defined by first and second electrodes 502 and 504, respectively. The first electrode 502 is an inner electrode that is approximately circular in cross-section and that has a generally cylindrical outer surface. The second electrode 504 is an outer electrode having a generally cylindrical inner surface facing the outer surface of the first electrode 502. An electrically insulating material (not shown) supports the first electrode 502 and the second electrode 504 in an overlapping, spaced-apart arrangement one relative to the other. An annular space between the outer surface of the first electrode 502 and the inner surface of the second electrode 504 defines an analytical gap 506. The analytical gap 506 is of approximately uniform width and extends around the circumference of the first electrode 502. The first electrode 502 is in electrical communication with a not illustrated power supply, which during use is capable of applying a high voltage asymmetric waveform (DV) and a low voltage dc compensation voltage (CV) to the first electrode 502.

An ion inlet orifice 508 is provided through the second electrode 504 for introducing ions from an ion source into the analytical gap 506. The ion source may take the form of an electrospray ionization ion source 110 including a liquid delivery capillary 112 and a fine-tipped electrospray needle 114 that is held at high voltage relative to an adjacent surface. The electrospray needle 114 is contained within a not illustrated electrospray ionization (ESI) chamber. Adjacent to the ionization source is a curtain plate 116 serving as a counter-electrode for the electrospray needle 114. An orifice 118 within the curtain plate electrode 116 allows for transmission of ions that are produced at the electrospray needle 114 into a separate desolvation chamber 120. A flow of a desolvation gas is provided through gas inlet orifice 122 into the desolvation chamber 120, via a not illustrated gas conduit that is in communication with a desolvation gas source. A first portion of the desolvation gas, which is denoted in FIG. 5 using dotted lines, enters the analytical gap 506 and passes out through ion outlet orifice 510.

Referring still to FIG. 5, the orifice 118 within the curtain plate 116 allows a second portion of the desolvation gas, which is denoted in FIG. 5 using a solid line, to travel in a direction that is counter-current to the direction in which the ions are moving within the desolvation chamber 120, so as to desolvate the ions before they are introduced into the analytical gap 506. The second portion of the desolvation gas exits the not illustrated ESI chamber via a gas outlet orifice thereof, thereby removing solvent vapor and minimizing the introduction of neutral species into the analytical gap 506. By way of a specific and non-limiting example, the desolvation gas that is provided into the desolvation chamber 120 via the gas inlet orifice 122 is substantially nitrogen gas ($N_2$).

A separate carrier gas conduit 512 is provided through a portion of the second electrode 504 and opening into the analytical gap 506 at a location that is between a barrier element 514 and the ion inlet orifice 508. The barrier element 514 is fabricated from an electrically insulating material and makes a gas-tight seal between the first electrode 502 and the second electrode 504, such that a flow of gas introduced via the carrier gas conduit 512 is directed preferentially in one direction around the analytical gap 506, as denoted using the dashed line in FIG. 5, toward the ion outlet orifice 510. By way of a specific and non-limiting example, the carrier gas conduit 512 is in fluid communication with a source of helium gas (He). The helium gas flows within the second electrode 504 via the carrier gas conduit 512 and out into the analytical gap 506, where it mixes with the first portion of the desolvation gas, thereby forming a mixed gas flow within the analytical gap 506.

During use, the mixed gas flow transports not illustrated ions through an electric field that is formed within the analytical gap 506 by the application of the DV and the CV to the first electrode 502. Ion separation occurs within the analytical gap 506 on the basis of the high field mobility properties of the ions. Those ions that have a stable trajectory for a particular combination of DV and CV are selectively transmitted through the analytical gap 506, whilst other ions collide with an electrode surface and are lost. The selectively transmitted ions are extracted from the analytical gap 506 via the ion outlet orifice 510.

In FIG. 5, ions that are produced at the electrospray needle 114 are caused to travel downstream along an ion flow path through the desolvation chamber 120, into analytical gap 506 and eventually out through ion outlet orifice 510. The gas conduit 512 provides a flow of carrier gas, such as for instance He, via an outlet end thereof that is open adjacent to a portion of the ion flow path that is defined downstream relative to the desolvation chamber 120. In the specific example that is shown in FIG. 5, the portion of the ion flow path that is defined downstream relative to the desolvation chamber is within analytical gap 506. The flow of carrier gas is provided directly into analytical gap 506 and barrier element 514 causes the flow to travel in one direction only, such that the flow of carrier gas encounters and mixes with the desolvation gas entering via ion inlet orifice 508, which is downstream relative to the desolvation chamber 120. Since the He gas exiting the gas conduit 512 is preferentially directed into the analytical gap 506, a total flow of only 250 mL/min He is required during operation of the FAIMS apparatus 500. By adjusting the flow of $N_2$ desolvation gas being introduced into the desolvation chamber 120 via gas inlet orifice 122, a total flow of 500 mL 50:50 He:$N_2$ still is achievable through the analytical gap. Advantageously, a flow of relatively inexpensive $N_2$ gas is used to desolvate the ions that are produced at electrospray needle 114. Of course, the numerical values that are provided in this example are intended to be illustrative in nature. The actual He gas savings depend on many characteristics of the FAIMS apparatus 500 being considered relative to the prior art FAIMS apparatus 100.

Figure 6:
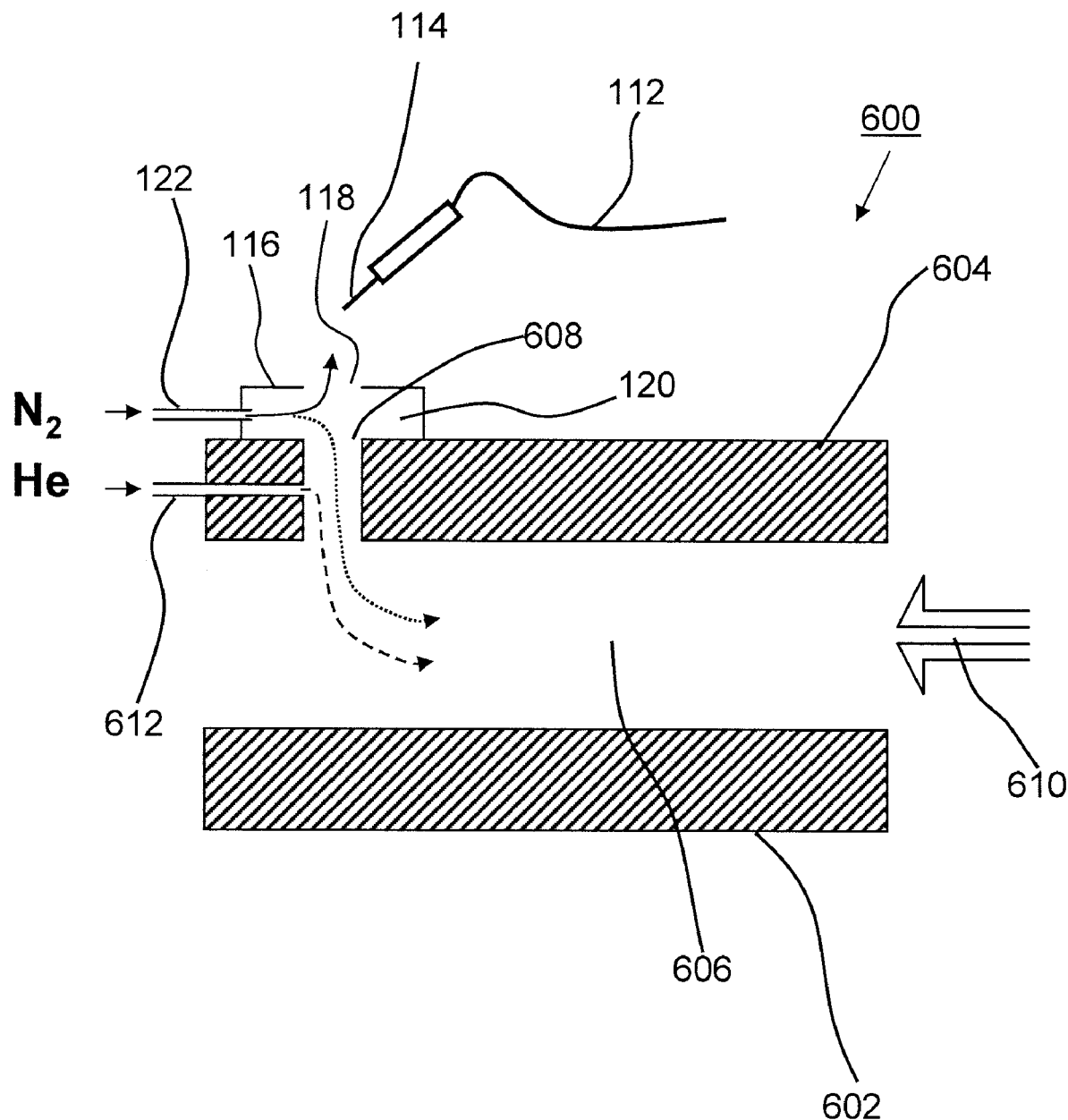
FIG. 6 is a simplified cross-sectional view showing a flat-plate geometry FAIMS or a cylindrical d-FAIMS apparatus according to an embodiment of the instant invention; and, FIG. 7 is a simplified flow diagram for a method according to an embodiment of the instant invention.

Referring now to FIG. 6, shown is a simplified cross-sectional view of a flat-plate geometry FAIMS or a cylindrical d-FAIMS apparatus according to an embodiment of the instant invention. Since the details of the gas inlet system and ion inlet system are substantially the same in both cases, the discussion relating to the apparatus shown in FIG. 6 is equally applicable to either of the flat-plate or d-FAIMS apparatus. The FAIMS shown generally at 600 includes first and second electrodes 602 and 604, respectively. An electrically insulating material (not shown) supports the first electrode 602 and the second electrode 604 in a spaced-apart, facing arrangement one relative to the other. A space between the first electrode 602 and the second electrode 604 defines an analytical gap 606. The analytical gap 606 is of approximately uniform width. The first electrode 602 is in electrical communication with a not illustrated power supply, which during use is capable of applying a high voltage asymmetric waveform (DV) and a low voltage dc compensation voltage (CV) to the first electrode 602.

An ion inlet orifice 608 is provided through the second electrode 604 for introducing ions from an ion source into the analyzer region 606. The ion source may take the form of an electrospray ionization ion source 110 including a liquid delivery capillary 112 and a fine-tipped electrospray needle 114 that is held at high voltage relative to an adjacent surface. The electrospray needle 114 is contained within a not illustrated electrospray ionization (ESI) chamber. Adjacent to the ionization source is a curtain plate 116 serving as a counter-electrode for the electrospray needle 114. An orifice 118 within the curtain plate electrode 116 allows for transmission of ions that are produced at the electrospray needle 114 into a separate desolvation chamber 120. A flow of a desolvation gas is provided through a gas inlet orifice 122 into the desolvation chamber 120. A first portion of the desolvation gas, which is denoted in FIG. 6 using dotted lines, enters the analytical gap 606 passes out through ion outlet orifice 610.

Referring still to FIG. 6, the orifice 118 within the curtain plate 116 allows for a second portion of the desolvation gas, which is denoted in FIG. 6 using a solid line, to travel in a direction that is counter-current to the direction in which the ions are moving within the desolvation chamber 120, so as to desolvate the ions before they are introduced into the analytical gap 606. The second portion of the flow of gas exits the not illustrated ESI chamber via a gas outlet orifice thereof, thereby removing solvent vapor and minimizing the introduction of neutral species into the analytical gap 606. By way of a specific and non-limiting example, the desolvation gas that is provided into the desolvation chamber 120 via the gas inlet orifice 122 is substantially nitrogen gas ($N_2$).

A separate gas conduit 612 is provided through a portion of the second electrode 604 and opening into the ion inlet orifice 608. A flow of a carrier gas is provided via the gas conduit 612 directly into the ion inlet orifice 608, as denoted using the dashed line in FIG. 6. By way of a specific and non-limiting example, an end of the gas conduit 612 that is opposite the ion inlet orifice end is in fluid communication with a source of helium gas (He). By adjusting the relative flow rates of the $N_2$ gas and of the He gas, the He gas exiting the gas conduit 612 is directed preferentially into the analytical gap 606 where it mixes with the first portion of the desolvation gas, thereby forming a mixed gas flow within the analytical gap 606. During use, the mixed gas flow transports the not illustrated ions through an electric field that is formed within the analytical gap 606 by the application of the DV and the CV to the first electrode 602. Ion separation occurs within the analytical gap 606 on the basis of the high field mobility properties of the ions. Those ions that have a stable trajectory for a particular combination of DV and CV are selectively transmitted through the analytical gap 606, whilst other ions collide with an electrode surface and are lost. The selectively transmitted ions are extracted from the analytical gap 606 via the ion outlet orifice 610.

In FIG. 6, ions that are produced at the electrospray needle 114 are caused to travel downstream along an ion flow path through the desolvation chamber 120, into analytical gap 606 and eventually out through ion outlet orifice 610. The gas conduit 612 provides a flow of carrier gas, such as for instance He, via an outlet end thereof that is open adjacent to a portion of the ion flow path that is defined downstream relative to the desolvation chamber 120. In the specific example that is shown in FIG. 6, the portion of the ion flow path that is defined downstream relative to the desolvation chamber is within the ion inlet orifice 608. Assuming that the He gas exiting the gas conduit 612 is preferentially directed into the analytical gap 606, a total flow of only 250 mL/min He is required during operation of the FAIMS apparatus 600. By adjusting the flow of $N_2$ desolvation gas being introduced into the desolvation chamber 120 via gas inlet orifice 122, a total flow of 500 mL 50:50 He:$N_2$ still is achievable through the analytical gap. Advantageously, a flow of relatively inexpensive $N_2$ gas is used to desolvate the ions that are produced at electrospray needle 114. Of course, the numerical values that are provided in this example are intended to be illustrative in nature. The actual He gas savings depend on many characteristics of the FAIMS apparatus 600 being considered relative to the prior art FAIMS apparatus 100.

Figure 7:
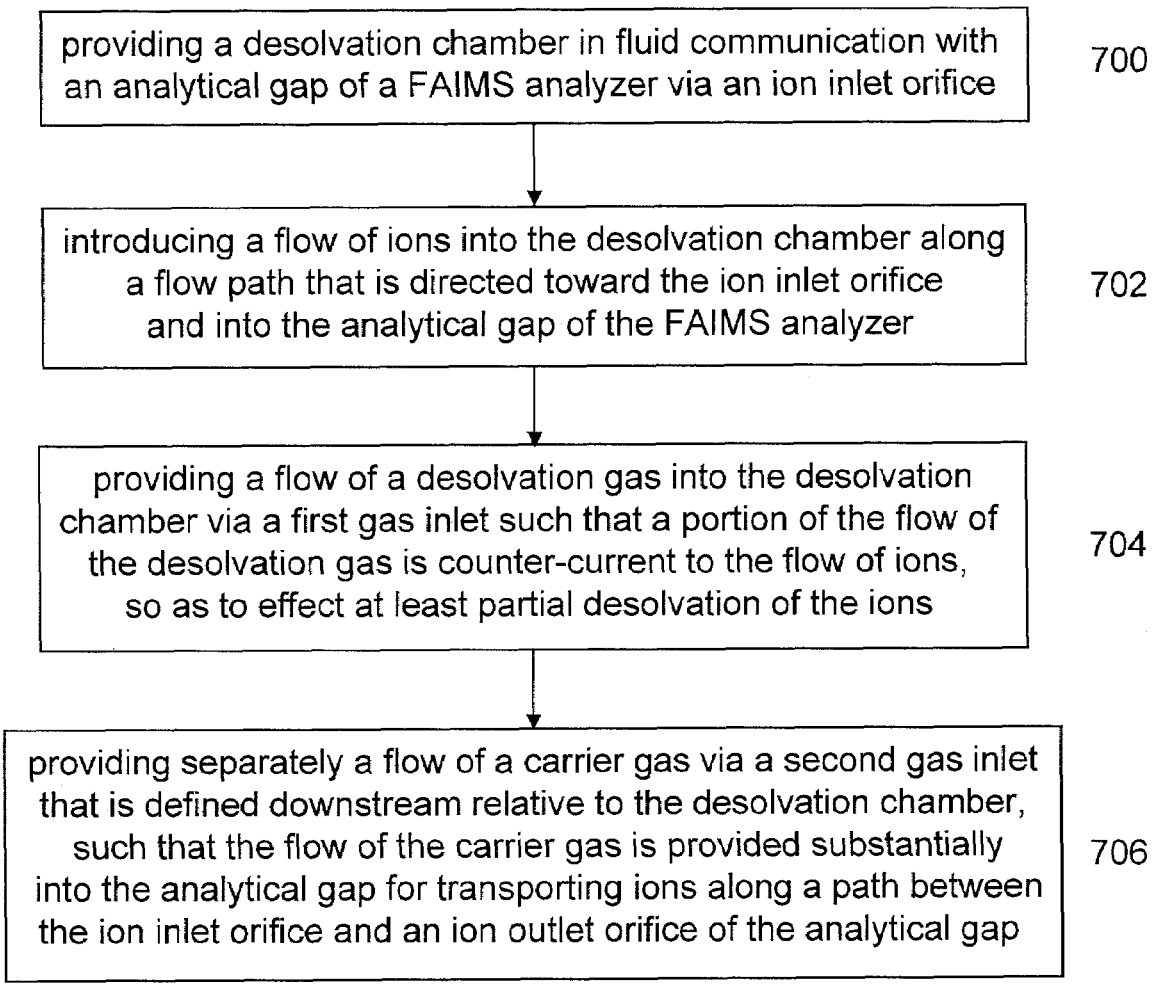

Referring now to FIG. 7, shown is a simplified flow diagram for a method according to an embodiment of the instant invention. At step 700 a desolvation chamber is provided, which is in fluid communication with an analytical gap of a FAIMS analyzer via an ion inlet orifice. At step 702 a flow of ions is introduced into the desolvation chamber along a flow path that is directed toward the ion inlet orifice and into the analytical gap of the FAIMS analyzer. At step 704 a flow of a desolvation gas is provided into the desolvation chamber via a first gas inlet, such that a portion of the flow of the desolvation gas is counter-current to the flow of ions. In this way the ions are at least partially desolvated. At step 706 a flow of a carrier gas is provided separately via a second gas inlet, which is defined downstream relative to the desolvation chamber. The flow of carrier gas is provided substantially into the analytical gap, for transporting ions along a path between the ion inlet orifice and an ion outlet orifice of the analytical gap.

Referring still to the method of FIG. 7, the composition of the desolvation gas is different than the composition of the carrier gas. During use the carrier gas mixes with a portion of the desolvation gas so as to form a mixed gas-flow within the analytical gap. In an optional step, a desolvation gas flow rate is selected and a carrier gas flow rate is selected for achieving a predetermined gas composition of the mixed gas-flow within the analytical gap. The method of FIG. 7 may be used in connection with a FAIMS apparatus according to any one of FIGS. 2a, 3a, 4a, 5a and 6a. In the FAIMS apparatus that is disclosed in connection with any of the above-mentioned figures, the analytical gap is defined by a space between first and second spaced-apart electrodes and the second gas inlet defines one end of a gas conduit that is defined within a portion of the second electrode. Accordingly, the method of FIG. 7 includes providing the flow of the carrier gas through the portion of the second electrode via the gas conduit.

While the various embodiments of the FAIMS apparatus have been described and depicted herein as being operated in conjunction with electrospray ionization (ESI) sources, it should be recognized that a FAIMS apparatus constructed in accordance with the present invention may be beneficially utilized in conjunction with a variety of ionization sources, including but not limited to atmospheric pressure chemical ionization (APCI) and atmospheric pressure photoionization (APPI) sources.

It should also be recognized that the compositions and flow rates of the desolvation and carrier gases may be varied from the illustrative examples presented above without departing from the scope of the present invention, e.g., in certain implementations a mixture of helium and nitrogen gas may be utilized as the carrier gas in place of pure helium, or the relative flow rates of the carrier and desolvation gases may be varied from the values given above such that the helium:nitrogen ratio within the analytical region is less or greater than 50:50.

Numerous other embodiments may be envisaged without departing from the spirit and scope of the invention.

What is claimed is:

1. A field asymmetric ion mobility spectrometer (FAIMS) apparatus comprising:
   an ionization source for producing ions from a sample;
   an analyzer region comprising a first electrode and a second electrode disposed in a spaced-apart facing relationship one relative to the other so as to define an analytical gap therebetween, there being an ion inlet orifice defined through a first portion of the second electrode for supporting ion introduction into the analytical gap;
   a desolvation chamber disposed intermediate the ionization source and the analyzer region, such that ions that are produced by the ionization source travel downstream along an ion flow path through the desolvation chamber and into the analytical gap via the ion inlet orifice;
   a first gas conduit extending between an inlet end that is coupleable to a desolvation gas source and an outlet end that opens into the desolvation chamber, the first gas conduit for providing a flow of a desolvation gas into the desolvation chamber; and,
   a second gas conduit extending through a portion of the second electrode and between an inlet end that is couplable to a carrier gas source and an outlet end that is open adjacent to a portion of the ion flow path that is defined downstream relative to the desolvation chamber, the second gas conduit for providing a flow of a carrier gas separately from the flow of the desolvation gas,
   wherein the composition of the desolvation gas is different than the composition of the carrier gas, and
   wherein the outlet of the second gas conduit is in communication with a circumferential gas-flow distributing element that is recessed within a portion of a sidewall surface of the ion inlet orifice.

2. A field asymmetric ion mobility spectrometer (FAIMS) apparatus comprising:
   an ionization source for producing ions from a sample;
   an analyzer region comprising a first electrode and a second electrode disposed in a spaced-apart facing relationship one relative to the other so as to define an analytical gap therebetween, there being an ion inlet orifice defined through a first portion of the second electrode for supporting ion introduction into the analytical gap;
   a desolvation chamber disposed intermediate the ionization source and the analyzer region, such that ions that are produced by the ionization source travel downstream along an ion flow path through the desolvation chamber and into the analytical gap via the ion inlet orifice;
   a first gas conduit extending between an inlet end that is coupleable to a desolvation gas source and an outlet end that opens into the desolvation chamber, the first gas conduit for providing a flow of a desolvation gas into the desolvation chamber; and,
   a second gas conduit extending through a portion of the second electrode between an inlet end that is coupleable to a carrier gas source and an outlet end that is defined within a portion of a sidewall surface of the ion inlet orifice and that is open adjacent to a portion of the ion flow path that is defined downstream relative to the desolvation chamber, the second gas conduit for providing a flow of a carrier gas separately from the flow of the desolvation gas,
   wherein the composition of the desolvation gas is different than the composition of the carrier gas.

3. A FAIMS apparatus according to claim 2, wherein the first electrode and the second electrode each comprises a flat plate electrode.

4. FAIMS apparatus according to claim 2, wherein the analytical gap is a generally annular space defined between the first electrode and the second electrode.

5. A FAIMS apparatus according to claim 2, wherein a portion of the second gas conduit proximate the outlet end thereof is angled in a direction toward the analytical gap and away from the desolvation chamber, such that a flow of carrier gas exiting from the first end of the gas conduit is directed preferentially toward the analytical gap.

6. A field asymmetric ion mobility spectrometer (FAIMS) apparatus comprising:
   a desolvation chamber for receiving ions from an ionization source, there being a first gas inlet defined through a portion of the desolvation chamber for supporting introduction of a flow of a desolvation gas into the desolvation chamber;
   a first electrode having a first electrode surface;
   a second electrode having a second electrode surface, the second electrode being spaced-apart from the first electrode and disposed relative to the first electrode such that the second electrode surface faces the first electrode surface so as to define an analytical gap therebetween, an ion inlet orifice being defined within a portion of the second electrode for providing fluid communication between the desolvation chamber and the analytical gap, the ion inlet orifice for receiving ions into the analytical gap, the second electrode further comprising a gas conduit defined through a portion thereof and extending between a first end that opens into the ion inlet orifice and a second end that is in communication with a source of a carrier gas, for providing a flow of a carrier gas separately from the flow of the desolvation gas,
   wherein the first end of the gas conduit is in communication with a circumferential gas-flow distributing element that is recessed within a portion of a sidewall surface of the ion inlet orifice.

7. A FAIMS apparatus according to claim 6, wherein the composition of the desolvation gas is different than the composition of the carrier gas.

8. A FAIMS apparatus according to claim 6, wherein the first electrode and the second electrode each comprises a flat plate electrode.

9. A FAIMS apparatus according to claim 6, wherein the analytical gap is a generally annular space defined between the first electrode surface and the second electrode surface.

10. A method for analyzing ions, comprising:
    providing a desolvation chamber that is in fluid communication with an analytical gap of a FAIMS analyzer via an ion inlet orifice, the analytical gap being defined by a space between first and second spaced-apart electrodes;
    introducing a flow of ions into the desolvation chamber along a flow path that is directed toward the ion inlet orifice and into the analytical gap of the FAIMS analyzer;
    providing a flow of a desolvation gas into the desolvation chamber via a first gas inlet such that a portion of the flow of the desolvation gas is counter-current to the flow of ions, so as to effect at least partial desolvation of the ions; and
    providing separately a flow of a carrier gas through a portion of the second electrode via a gas conduit that is defined within the portion of the second electrode and through a portion of a sidewall surface of the ion inlet orifice via a second gas inlet, the second gas inlet defining one end of the gas conduit and being defined downstream relative to the desolvation chamber within the portion of the sidewall surface of the ion inlet orifice, wherein the composition of the carrier gas is different than the composition of the desolvation gas, and the flow of the carrier gas is provided substantially into the analytical gap for transporting ions along a path between the ion inlet orifice and an ion outlet orifice of the analytical gap.

11. A method according to claim 10, wherein the carrier gas mixes with a portion of the desolvation gas so as to form a mixed gas-flow within the analytical gap.

12. A method according to claim 11, comprising selecting a desolvation gas flow rate and selecting a carrier gas flow rate for achieving a predetermined gas composition of the mixed gas-flow within the analytical gap.

13. A field asymmetric ion mobility spectrometer (FAIMS) apparatus, comprising:
a desolvation chamber for receiving ions from an ionization source, there being a first gas inlet defined through a portion of the desolvation chamber for supporting introduction of a flow of a desolvation gas into the desolvation chamber;
a first electrode having a first electrode surface;
a second electrode having a second electrode surface, the second electrode being spaced-apart from the first electrode and disposed relative to the first electrode such that the second electrode surface faces the first electrode surface so as to define an analytical gap therebetween, an ion inlet orifice being defined within a portion of the second electrode for providing fluid communication between the desolvation chamber and the analytical gap, the ion inlet orifice for receiving ions into the analytical gap, the second electrode further comprising a gas conduit defined through a portion thereof and extending between a first end that is defined within a portion of a sidewall surface of the ion inlet orifice and a second end that is in communication with a source of a carrier gas, for providing a flow of a carrier gas separately from the flow of the desolvation gas.

14. A FAIMS apparatus according to claim 13, wherein the first end of the gas conduit is in communication with a circumferential gas-flow distributing element that is recessed within a portion of the sidewall surface of the ion inlet orifice.

15. A FAIMS apparatus according to claim 13, wherein the first electrode and the second electrode each comprises a flat plate electrode.

16. A FAIMS apparatus according to claim 13, wherein the analytical gap is a generally annular space defined between the first electrode and the second electrode.

17. A FAIMS apparatus according to claim 13, wherein a portion of the gas conduit proximate the first end thereof is angled in a direction toward the analytical gap and away from the desolvation chamber, such that a flow of carrier gas exiting from the first end of the gas conduit is directed preferentially toward the analytical gap.

18. A FAIMS apparatus according to claim 13, wherein the composition of the desolvation gas is different than the composition of the carrier gas.

* * * * *